(12) United States Patent
Tsubota et al.

(10) Patent No.: US 8,334,516 B2
(45) Date of Patent: Dec. 18, 2012

(54) RADIATION DETECTING APPARATUS, RADIOGRAPHIC IMAGE CAPTURING SYSTEM, AND RADIOGRAPHIC IMAGE CAPTURING METHOD

(75) Inventors: Keiji Tsubota, Minami-ashigara (JP); Masato Hattori, Minami-ashigara (JP); Yutaka Yoshida, Fuchu (JP); Yasunori Ohta, Yokohama (JP); Naoyuki Nishino, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 452 days.

(21) Appl. No.: 12/659,836

(22) Filed: Mar. 23, 2010

(65) Prior Publication Data
US 2010/0243910 A1  Sep. 30, 2010

(30) Foreign Application Priority Data

Mar. 24, 2009 (JP) ................................ 2009-072379
Mar. 8, 2010 (JP) ................................ 2010-050889

(51) Int. Cl.
*G01T 1/24* (2006.01)

(52) U.S. Cl. .................................. 250/370.08; 250/395
(58) Field of Classification Search ............... 250/336.1, 250/370.01, 370.08, 370.09, 393, 395, 580; 378/98.8, 114, 189
See application file for complete search history.

(56) References Cited

FOREIGN PATENT DOCUMENTS

| JP | 2000-105297 | 4/2000 |
|---|---|---|
| JP | 3494683 | 11/2003 |
| JP | 2008-170315 | 7/2008 |

*Primary Examiner* — Mark R Gaworecki
(74) *Attorney, Agent, or Firm* — Jean C. Edwards, Esq.; Edwards Neils PLLC

(57) ABSTRACT

A radiographic image capturing system includes an image capturing apparatus for applying radiation to a subject, a radiation detecting apparatus for detecting radiation transmitted through the subject, a power feeder for supplying electric power contactlessly to a contactless power receiver of the radiation detecting apparatus, a feeding-state determining unit for determining whether power-feeding by the power feeder is being performed or not, and a signal generator for generating an image-capturing inhibition signal for inhibiting radiographic image-capturing by the image capturing apparatus if the feeding-state determining unit judges that the power-feeding is being performed.

15 Claims, 15 Drawing Sheets

US 8,334,516 B2

RADIATION DETECTING APPARATUS, RADIOGRAPHIC IMAGE CAPTURING SYSTEM, AND RADIOGRAPHIC IMAGE CAPTURING METHOD

CROSS-REFERENCE TO RELATED APPLICATION

This application is based upon and claims the benefit of priority from Japanese Patent Applications No. 2009-072379 filed on Mar. 24, 2009 and No. 2010-050889 filed on Mar. 8, 2010, of which the contents are incorporated herein by reference.

BACKGROUND OF THE INVENTION

1. Field of the Invention

The present invention relates to a radiation detecting apparatus having a radiation detector for detecting radiation which has passed through a subject and a contactless power receiver, a radiographic image capturing system having a contactless power feeder for contactlessly supplying electric power to such a radiation detecting apparatus, and a radiographic image capturing method.

2. Description of the Related Art

In the medical field, there have widely been used radiographic image capturing apparatus, which apply radiation to a subject and guide the radiation that has passed through the subject to a radiation conversion panel, which captures a radiographic image from the radiation. Known forms of the radiation conversion panel include a conventional radiation film for recording a radiographic image by way of exposure, and a stimulable phosphor panel for storing radiation energy representing a radiographic image in a phosphor and reproducing the radiographic image as stimulated light by applying stimulating light to the phosphor. The radiation film with the recorded radiographic image is supplied to a developing device to develop the radiographic image, or the stimulable phosphor panel is supplied to a reading device to read the radiographic image as a visible image.

In the operating room or the like, it is necessary to read and display a recorded radiographic image immediately from a radiation conversion panel after the radiographic image has been captured for the purpose of quickly and appropriately treating the patient. Patients such as infants, children, aged people, or those who cannot stand themselves for a long time due to illness or injuries also need to be imaged quickly. As a radiation conversion panel which meets such a requirement, there has been developed a direct-conversion-type radiation detector for converting radiation directly into electric signals or an indirect-conversion-type radiation detector for converting radiation into visible light with a scintillator and then converting the visible light into electric signals with a solid-state detector to read a detected radiographic image.

Japanese Laid-Open Patent Publication No. 2008-170315 discloses a radiation detecting apparatus (electronic cassette) having a function to transmit radiographic image information produced by a radiation detector to an image processor or the like via a wireless transmission system. The electronic cassette incorporates a battery therein. For charging the battery, the electronic cassette is mounted on a separate cradle having a contactless battery charger. The battery is wirelessly charged by the contactless battery charger while the electronic cassette is being mounted on the cradle.

According to the radiation detecting apparatus disclosed in Japanese Laid-Open Patent Publication No. 2008-170315, when the remaining power level of the battery of an electronic cassette in current use runs low after the radiation detecting apparatus has been used to capture a plurality of radiographic images of many patients or a patient during a surgical operation on the patient or when the remaining power level of the battery runs low right after charging because the battery is end-of-life, it is necessary to remove the electronic cassette from under the patient, bring the electronic cassette to the cradle, and charge the battery in the electronic cassette that is mounted on the cradle. However, such a charging process is troublesome and possibly tends to make the surgical operation time-consuming and be burdensome to the patient.

In order to solve the above problem, contactless (wireless) power feeding is effective, in which a battery can be charged on the spot without moving to the cradle. However, in this case, electromagnetic wave generated in the contactless feeding may affect minute analog signals of a radiation detector adversely. If a radiographic image is captured while the battery of the electronic cassette is contactlessly charged, noise caused by magnetic fluxes used for the contactless power feeding is liable to adversely affect the radiographic image information. As a result, it is highly possible for the radiation detecting apparatus to fail to acquire high-quality radiographic images. At worst, noise-induced artifact and adverse effect on the radiographic image may result in erroneous diagnosis and erroneous decision during an operation.

SUMMARY OF THE INVENTION

It is an object of the present invention to provide a radiation detecting apparatus, a radiographic image capturing system, and a radiographic image capturing method which make it possible to supply electric power to the radiation detecting apparatus with ease and also to acquire high-quality radiographic images.

A radiation detecting apparatus according to the present invention comprises a radiation detector for detecting radiation transmitted through a subject and converting the detected radiation into radiographic image information, a power supply for supplying electric power to the radiation detector, a contactless power receiver for receiving electric power supplied contactlessly from an external contactless power feeder and supplying the received electric power to the power supply, a feeding-state determining unit for determining whether power-feeding by the contactless power feeder is being performed or not, and an image-capturing operation processing unit for performing a process for invalidating an operation for image-capturing by the radiation at least if the feeding-state determining unit judges that the power-feeding is being performed.

A radiographic image capturing system according to the present invention comprises a radiation applying apparatus for applying radiation to a subject, a radiation detecting apparatus including a radiation detector for detecting the radiation transmitted through the subject and converting the detected radiation into radiographic image information, and a power supply for supplying electric power to the radiation detector, a contactless power feeder disposed in the radiation detecting apparatus, for supplying electric power contactlessly to a contactless power receiver which supplies electric power to the power supply, a controller for controlling the radiation applying apparatus, the radiation detecting apparatus, and the contactless power feeder, a feeding-state determining unit for determining whether power-feeding by the contactless power feeder is being performed or not, an image-capturing operation processing unit for performing a process for invalidating an operation for image-capturing by the radiation at least if the feeding-state determining unit judges that the power-feeding is being performed, and an image-capturing controller for controlling the radiation applying apparatus based on the process performed by the image-capturing operation processing unit.

With the above arrangement, while the radiation detecting apparatus with the radiation detector for detecting radiation and converting the radiation into radiographic image, e.g., an electronic cassette, is being held in a given image capturing position, the contactless power feeder can supply electric power to the radiation detecting apparatus with ease. Further, since the feeding-state determining unit for determining whether power-feeding by the contactless power feeder is being performed or not, and the image-capturing operation processing unit for performing a process for invalidating an operation for image-capturing by radiation at least if the feeding-state determining unit judges that the power-feeding is being performed, are provided, image-capturing during the power-feeding period can reliably be inhibited. Thus, the captured image is prevented from being adversely affected by noise due to the electric power supplied contactlessly by the contactless power feeder, thereby obtaining radiographic images of high-quality.

In the present invention, the image-capturing operation processing unit may generate an image-capturing inhibition signal for inhibiting the image-capturing by the radiation if the feeding-state determining unit judges that the power-feeding is being performed. Also, the image-capturing operation processing unit may not generate an image-capturing permission signal for permitting the image-capturing by the radiation if the feeding-state determining unit judges that the power-feeding is being performed.

Further, the image-capturing operation processing unit may generate an image-capturing permission signal for permitting the image-capturing by the radiation if the feeding-state determining unit judges that the power-feeding is not performed. With the arrangements, image-capturing can be started quickly after the power-feeding is finished during the image-capturing inhibition control.

Further, the radiation detector may comprise a storage device for storing the radiation as signal charges, and an A/D converter for converting the signal charges read from the storage device, into digital signals, and an image-capturing inhibition period during which image-capturing is inhibited based on the image-capturing inhibition signal, may include any one of, any combination of, or all of the following periods: a storage period during which the signal charges are stored in the storage device, a readout period during which the stored signal charges in the storage device are read out, and a conversion period during which the signal charges are converted into the digital signals by the A/D converter. With this arrangement, the captured images are more reliably prevented from being adversely affected by noise.

Also, the feeding-state determining unit and the image-capturing operation processing unit may be provided in at least one of the radiation applying apparatus, the radiation detecting apparatus, the contactless power feeder and the controller. With this arrangement, the image-capturing inhibition control during the power-feeding period can be performed more easily. Similarly, the image-capturing controller may be provided in at least one of the radiation applying apparatus, the radiation detecting apparatus, the contactless power feeder, and the controller. With this arrangement, the image-capturing inhibition control during the power-feeding period can be performed more easily.

The radiographic image capturing system may further include a display device for displaying the radiographic image information and indicating the inhibition of the image capturing.

In this case, the display device may indicate a present charged amount of the battery or a remaining charging time before the charged amount reaches an amount of electric power required for performing the image capturing. Further, the display device may indicate that there is another radiation detecting apparatus that has been already charged and has the amount of electric power required for performing the image capturing.

When such a display device is provided, a surgeon (doctor), a radiological technician or the like can easily grasp or judge whether image-capturing is inhibited at present or not, whether the battery is being charged or has been charged, and whether another radiation detecting apparatus should be used for the image-capturing or not.

According to the present invention, a method of capturing a radiographic image of a subject by applying radiation to the subject, detecting the radiation with a radiation detector of a radiation detecting apparatus, and converting the detected radiation into radiographic image information with the radiation detector, comprising the steps of supplying electric power contactlessly to a power supply of the radiation detecting apparatus, and inhibiting image-capturing by the radiation while power-feeding is being performed.

The above method reliably prevents image-capturing during power-feeding to the radiation detecting apparatus, e.g., electronic cassette. Thus, it is possible to prevent noise generated by electric power supplied contactlessly from a contactless power feeder from adversely affecting captured radiographic images, thereby acquiring radiographic images of high quality.

The above method may further comprise the step of starting the image-capturing after the power-feeding has been finished while the image-capturing is inhibited during the power-feeding. In this case, image-capturing can be resumed quickly. Incidentally, the meaning of "after the power-feeding has been finished" includes "immediately after contactless communication for power-feeding by the power feeder has been halted", "immediately after the contactless power receiver has stopped supply of electricity to the power supply", and the like.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
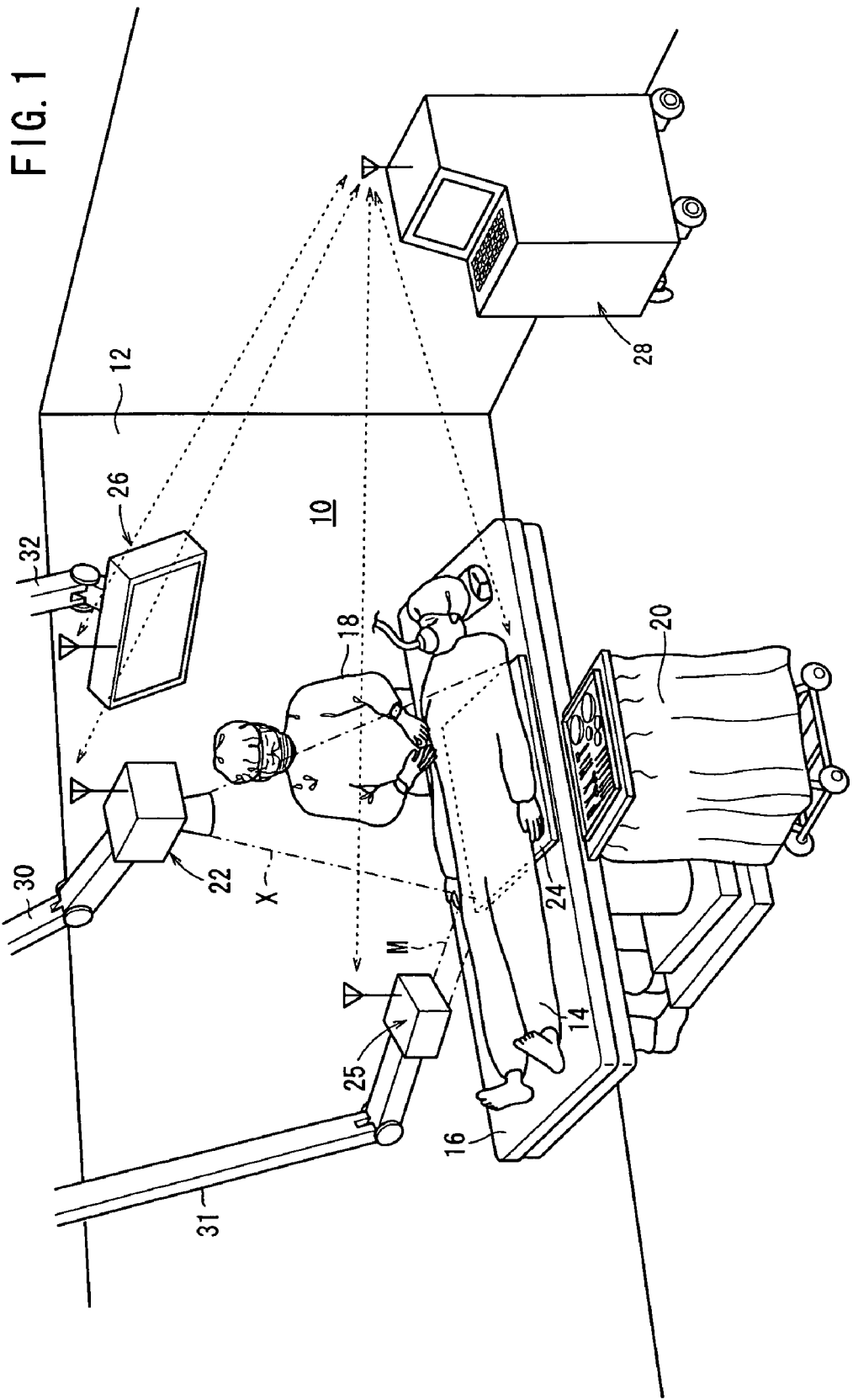
FIG. 1 is a perspective view of an operating room incorporating a radiographic image capturing system according to an embodiment of the present invention.

Like or corresponding parts are denoted by like or corresponding reference characters throughout views.

Radiographic image capturing systems and radiographic image capturing methods according to preferred embodiments of the present invention, in reference to radiation detecting apparatus used in the radiographic image capturing systems, will be described in detail below with reference to the accompanying drawings.

As shown in FIG. 1, an operating room 12 houses therein a radiographic image capturing system 10 (hereinafter also referred to as "image capturing system 10") according to an embodiment of the present invention. The operating room 12 houses, in addition to the radiographic image capturing system 10, a surgical table or bed 16 for a patient 14 to lie thereon, and an instrument table 20 disposed on one side of the surgical table 16 for placing thereon various tools and instruments to be used by a surgeon 18 for operating the patient 14. The surgical table 16 is surrounded by various apparatus required for surgical operations, including an anesthesia apparatus, an aspirator, an electrocardiograph, a blood pressure monitor, etc (not shown).

The image capturing system 10 includes an image capturing apparatus (radiation applying apparatus) 22 for irradiating the patient 14 as a subject with radiation X at a dose according to image capturing conditions, an electronic cassette (radiation detecting apparatus) 24 housing therein a radiation detector 40 (see FIG. 2) for detecting the radiation X that has passed through the patient 14, a power feeder (contactless power feeder, wireless power feeder) 25 for supplying electric power wirelessly (contactlessly) to a battery 44 (see FIG. 2) housed in the electronic cassette 24, a display device 26 for displaying a radiographic image based on the radiation X that has been detected by the radiation detector 40, and a console (controller) 28 for generally controlling the image capturing system 10. The image capturing apparatus 22, the electronic cassette 24, the power feeder 25, the display device 26, and the console 28 send and receive signals by way of wireless communications using UWB (Ultra Wide Band), WiFi (Wireless Fidelity) such as IEEE 802.11.a/g/n, or millimeter waves.

Since the power feeder 25 and the electronic cassette 24 are out of contact with each other, a contactless power feeding technique for feeding power contactlessly (wirelessly) is adopted as a technique for feeding power to (the battery 44 of) the electronic cassette 24 by the power feeder 25, as described above.

Specifically, the contactless power feeding technique includes (1) a microwave power feeding technique in which the power feeder 25 feeds power to the electronic cassette 24 using an electromagnetic wave in the microwave band, (2) an electromagnetic induction power feeding technique in which the power feeder 25 feeds power to the electronic cassette 24 by electromagnetic induction with the coil of the power feeder 25 being in proximity to the coil of the electronic cassette 24, and (3) a resonance power feeding technique in which the power feeder 25 feeds power to the electronic cassette 24 using electromagnetic resonance between the power feeder 25 and the electronic cassette 24.

Also, the above resonance power feeding technique (3) includes a magnetic resonance power feeding technique. In the magnetic resonance power feeding technique, the coils of the power feeder 25 and the electronic cassette 24 are adjusted to have substantially the same resonant frequency, and the coil of the power feeder 25 on the sending side generates electromagnetic field caused by high-frequency electric power in a given space of the operating room 12, while the coil of the electronic cassette 24 on the receiving side is placed in the generated electromagnetic field, whereby the coil of the electronic cassette 24 can receive the high-frequency electric power.

Incidentally, the contactless power feeding technique for feeding power to the electronic cassette 24 by the power feeder 25 (microwave type, electromagnetic induction type, resonance type, magnetic resonance type) can adopt a conventional contactless power feeding technique.

Hereinafter, if not otherwise specified, the power feeder 25 feeds power to the battery 44 of the electronic cassette 24 using a magnetic resonance power feeding technique.

The image capturing apparatus 22 is coupled to a universal arm 30 extending from the ceiling of the operating room 12 so as to be movable to a desired position for capturing an image of a desired area of the patient 14 and also to be retractable to a position out of the way while the surgeon 18 is performing a surgical operation on the patient 14. Similarly, the power feeder 25 is coupled to a universal arm 31 so as to be movable to a desired position depending on the location of the electronic cassette 24. The display device 26 is coupled to a universal arm 32 so as to be movable to a position where the surgeon 18 can easily confirm a captured radiographic image displayed on the display device 26. The universal arms 30, 31, 32 may alternatively be mounted on a wall, a floor, or a movable cart. The power feeder 25 and the display device 26 may alternatively be fixed to the ceiling, a wall, or a floor rather than being supported on the universal arms. The power feeder 25 should preferably be positioned horizontally laterally of the radiation detecting apparatus (the electronic cassette 24) (see FIGS. 1 and 12) or on the bottom side of the radiation detecting apparatus (see FIG. 13) so that a magnetic field M (electromagnetic field due to high-frequency electric power) applied from the power feeder 25 to the radiation detecting apparatus will be kept out of direct interference with the patient 14.

Figure 2:
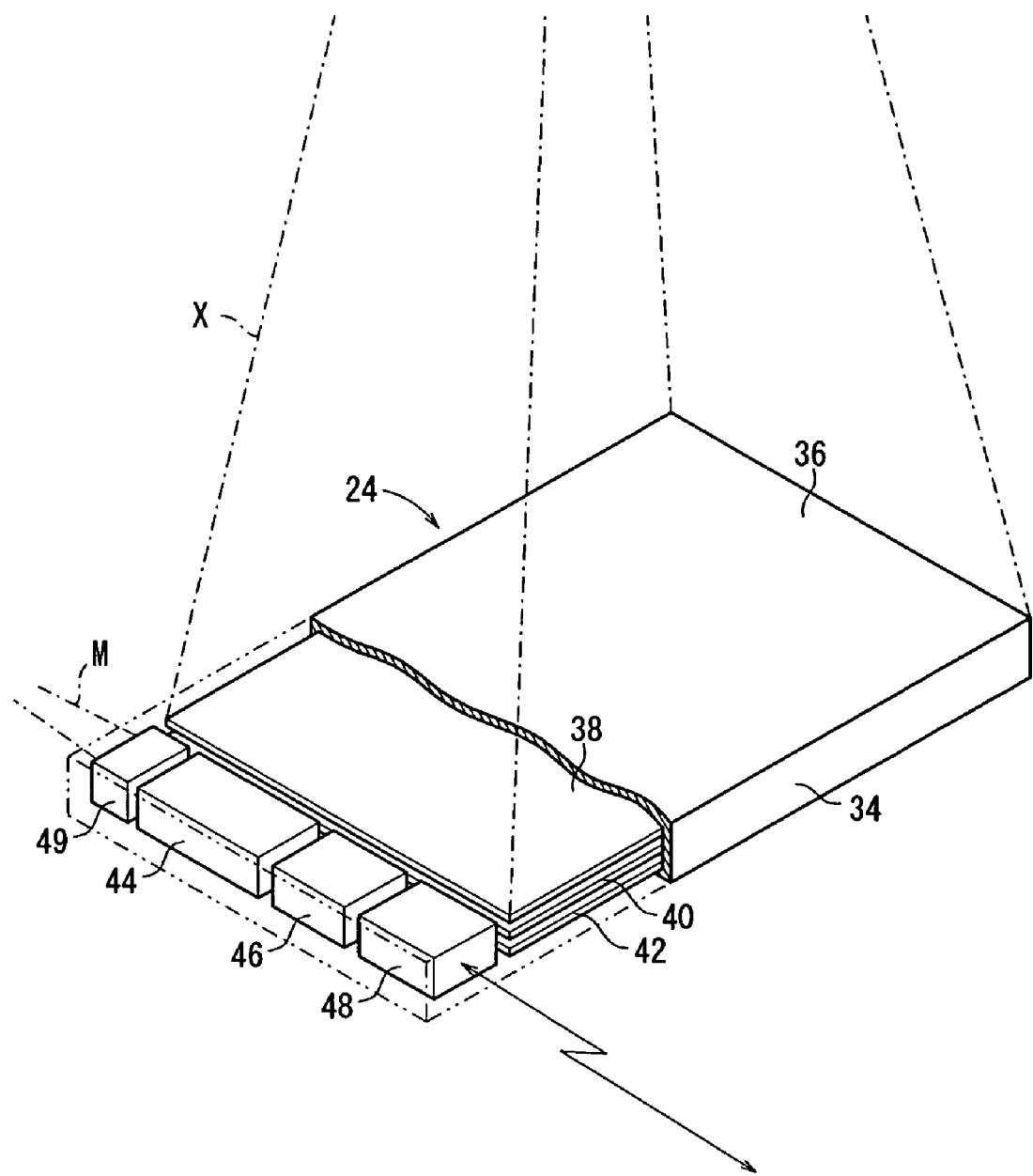
FIG. 2 is a perspective view, partly cut away, showing internal structural details of an electronic cassette used in the radiographic image capturing system shown in FIG. 1.

FIG. 2 shows in perspective internal structural details of the electronic cassette 24. As shown in FIG. 2, the electronic cassette 24 has a box-shaped casing 34 made of a material permeable to the radiation X. The casing 34 houses therein a grid 38 for removing scattered rays of the radiation X from the patient 14, a radiation detector (radiation conversion panel) 40 for detecting the radiation X that has passed through the patient 14, and a lead plate 42 for absorbing back scattered rays of the radiation X, which are successively arranged in the order named from a surface 36 of the casing 34 which is irradiated with the radiation X. The irradiated surface 36 of the casing 34 may be constructed as the grid 38.

The casing 34 also houses therein a battery 44 serving as a power supply of the electronic cassette 24, a cassette controller (image capturing controller) 46 for energizing the radiation detector 40 with electric power supplied from the battery 44, and a transceiver 48 for sending and receiving signals including the information of the radiation X (radiographic image information) detected by the radiation detector 40, to and from the console 28 by wireless communications. A shield plate of lead or the like should preferably be placed over the side surfaces of the battery 44, the cassette controller 46, and the transceiver 48 under the irradiated surface 36 of the casing 34 to protect the battery 44, the cassette controller 46, and the transceiver 48 against damage which would otherwise be caused if irradiated with the radiation X. The casing 34 also houses therein a wireless power receiver (contactless power receiver) 49 for receiving the magnetic field (magnetic fluxes) M converted from electric energy (high-frequency electric power) and applied contactlessly (wirelessly) by the power feeder 25, and converting the magnetic field M back into electric energy.

Figure 3:
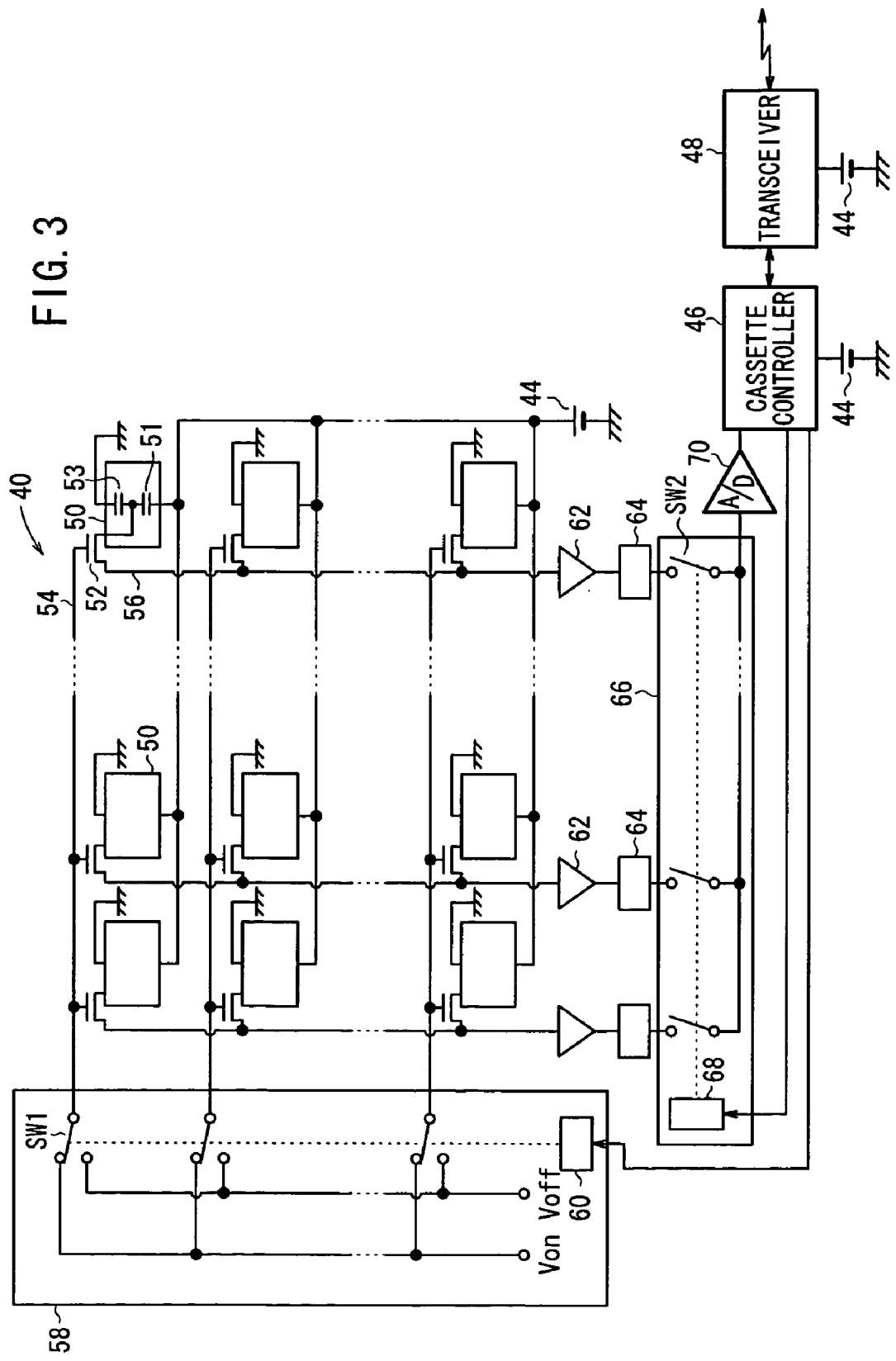
FIG. 3 is a block diagram of a circuit arrangement of a radiation detector in the electronic cassette shown in FIG. 2.

FIG. 3 shows in block form a circuit arrangement of the radiation detector 40. As shown in FIG. 3, the radiation detector 40 comprises a direct-conversion-type radiation detector. In this case, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed over the array of TFTs 52, and an array of storage capacitors (storage devices) 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its function at high temperatures, it needs to be used within a certain temperature range. Therefore, some means for cooling the radiation detector 40 should preferably be provided in the electronic cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter (A/D converting unit) 70. A radiographic image signal generated by the multiplexer 66 based on the electric charges from the sample and hold circuits 64 is converted by the A/D converter 70 into a digital image signal representing radiographic image information, which is supplied to the cassette controller 46.

The TFTs 52 which function as switching devices may be combined with another image capturing device such as a CMOS (Complementary Metal-Oxide Semiconductor) image sensor or the like. Alternatively, the TFTs 52 may be replaced with a CCD (Charge-Coupled Device) image sensor for shifting and transferring electric charges with shift pulses which correspond to gate signals in the TFTs.

Figure 4:
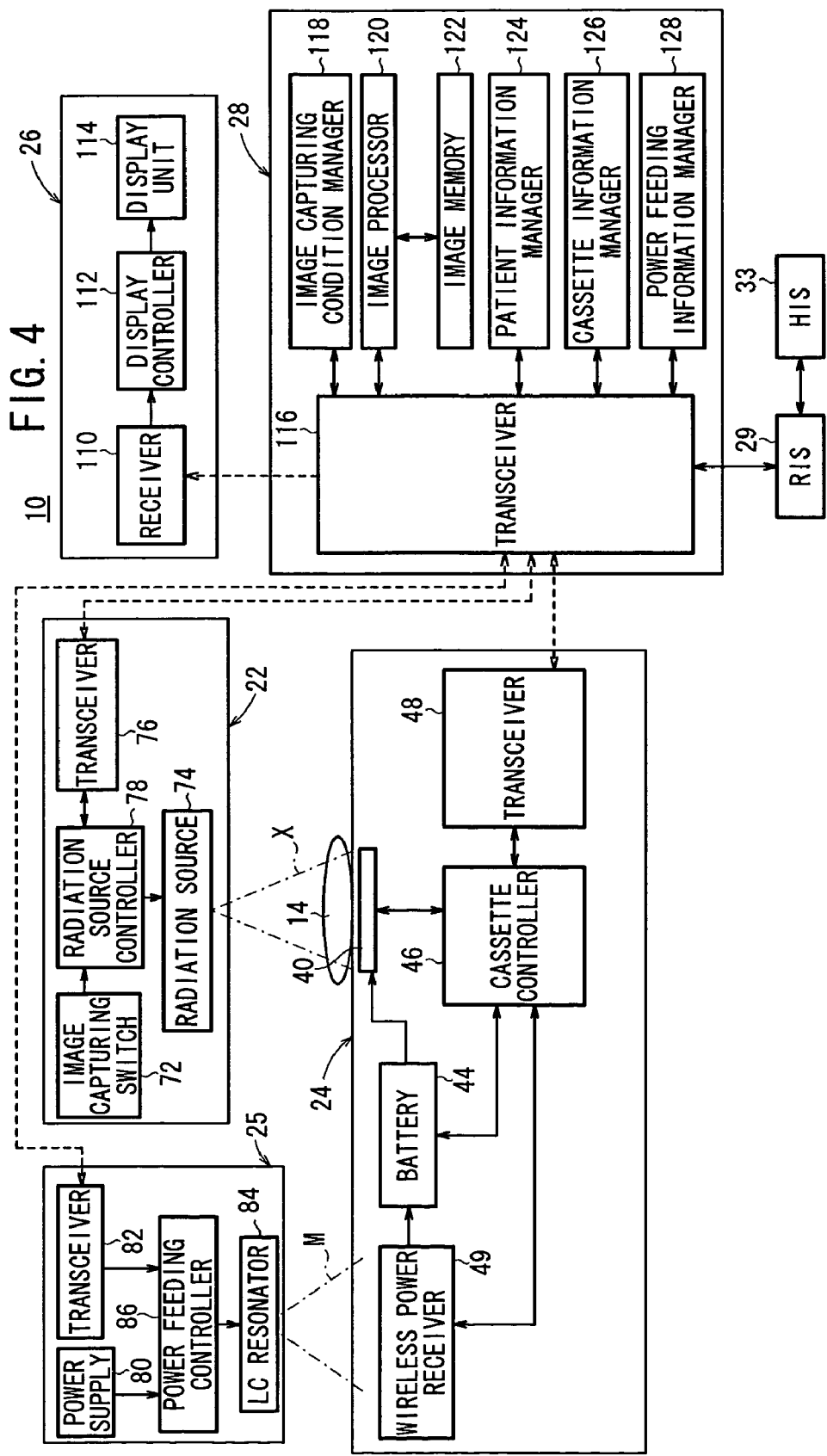
FIG. 4 is a block diagram of the radiographic image capturing system shown in FIG. 1.

FIG. 4 shows in block form the image capturing system 10 which comprises the image capturing apparatus 22, the electronic cassette 24, the power feeder 25, the display device 26, and the console 28.

The console 28 is connected to a radiology information system (RIS) 29 which generally manages radiographic image information handled by the radiological department of the hospital and other information. Also, the RIS 29 is connected to a hospital information system (HIS) 33 which generally manages medical information in the hospital.

The image capturing apparatus 22 comprises an image capturing switch 72, a radiation source 74, a transceiver 76, and a radiation source controller (image-capturing controller) 78. The transceiver 76 receives image capturing conditions from the console 28 by way of wireless communications and transmits an image capturing completion signal, etc. to the console 28 by way of wireless communications. The radiation source controller 78 controls the radiation source 74 based on an image capturing start signal supplied from the image capturing switch 72 and image capturing conditions supplied from the console 28. The radiation source 74 outputs the radiation X under the control of the radiation source controller 78.

The power feeder 25 comprises a power supply 80 connected to an external power supply or the like, not shown, a transceiver 82 for receiving a power feeding start signal, etc. from the console 28 by way of wireless communications and sending ID information (ID data), etc. of the power feeder 25 to the console 28 by way of wireless communications, an LC resonator (feeding unit) 84 for converting electric energy from the power supply 80 into the magnetic field M and applying the magnetic field M, or in other words, contactlessly (wirelessly) supplying electric energy, to the electronic cassette 24, and a power feeding controller (image-capturing controller) 86 for energizing the LC resonator 84 based on the power feeding start signal supplied from the console 28.

Figure 5:
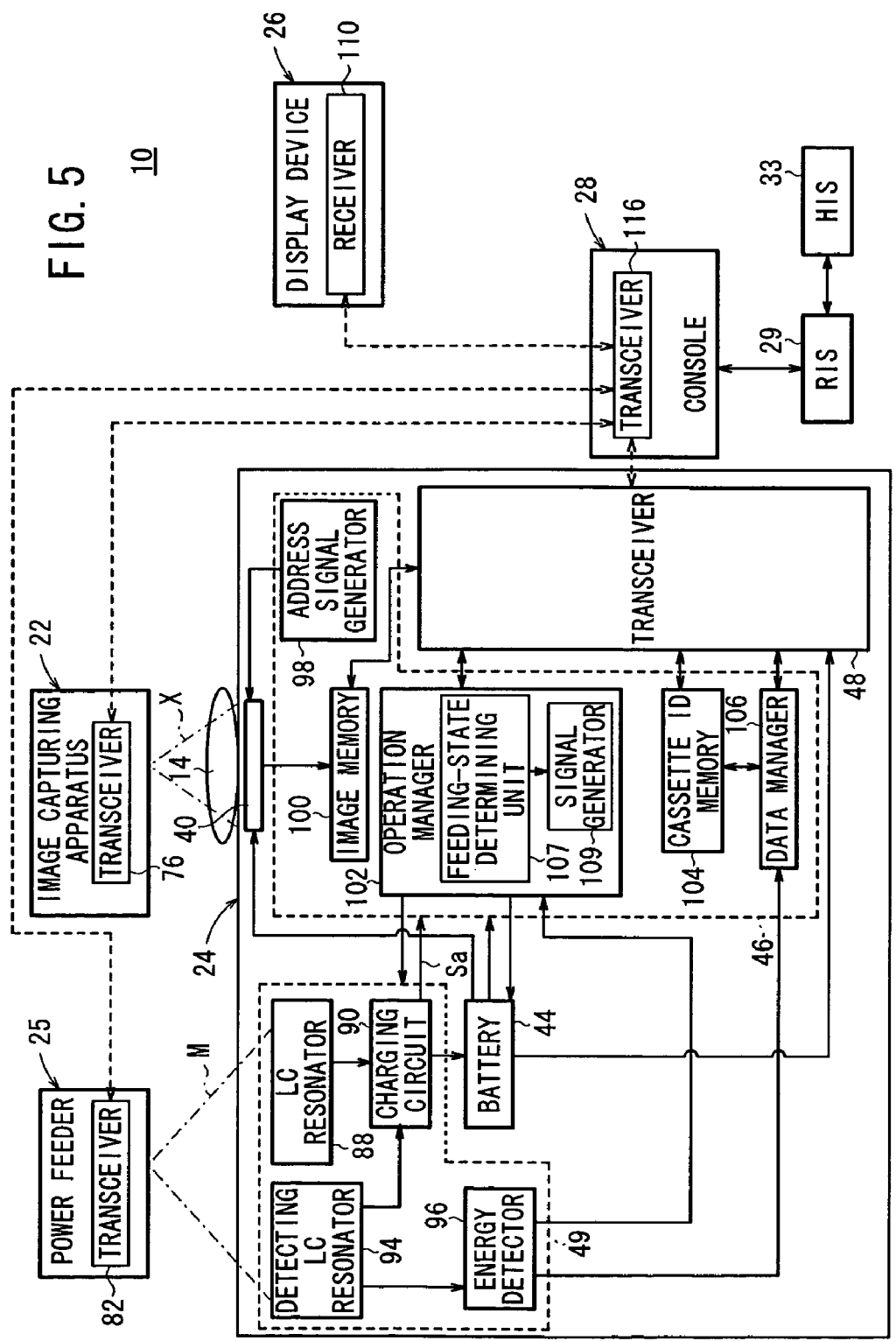
FIG. 5 is a block diagram of the radiographic image capturing system, showing structural details of the electronic cassette shown in FIG. 4.

FIG. 5 shows in block form the image capturing system 10, showing structural details of the electronic cassette 24 as the radiation detecting apparatus according to the present embodiment.

As shown in FIGS. 4 and 5, the electronic cassette 24 includes the radiation detector 40, the battery 44, the wireless power receiver 49, the cassette controller 46, and the transceiver 48.

The battery 44 comprises a chargeable secondary battery such as a lithium ion battery or the like, and serves as a power supply for supplying electric power to various parts of the electronic cassette 24, which include the radiation detector 40, the cassette controller 46, and the transceiver 48. The battery 44 may alternatively comprise an electric storage device such as an electric double layer capacitor or any of other devices insofar as it can be charged and serve as a power supply for the electronic cassette 24.

The wireless power receiver 49 has a function to receive the electric power contactlessly (wirelessly) supplied from the power feeder 25 and charge the battery 44 with the received electric power. The wireless power receiver 49 has an LC resonator 88 for receiving the magnetic field M applied from the LC resonator 84 of the power feeder 25 into electric energy (high-frequency power), and a charging circuit 90 for converting the electric energy from the LC resonator 88 into desired electric power and supplying the electric power to the battery 44. Specifically, the LC resonator 88 comprises an LC resonant circuit having a coil and a capacitor, and the charging circuit 90 rectifies the electric current generated by the LC resonator 88 into a constant electric current, and charges the battery 44 with the constant electric current. The charging circuit 90 outputs a signal Sa indicating that the charging circuit 90 is charging the battery 44, to the cassette controller 46 while the charging circuit 90 is converting the reconverted electric energy from the LC resonator 88, into a desired electric power. As a matter of course, the charging circuit 90 does not output the signal Sa unless the charging circuit 90 converts the reconverted electric energy from the LC resonator 88, into a desired electric power.

The wireless power receiver 49 also has a detecting LC resonator 94 disposed parallel to the LC resonator 88 and smaller in size than the LC resonator 88, and an energy detector 96 for detecting electric energy converted from the magnetic field M by the detecting LC resonator 94. The detecting LC resonator 94 also comprises an LC resonant circuit having a coil and a capacitor, as with the LC resonator 88. When the energy detector 96 detects the electric energy converted from the magnetic field M by the detecting LC resonator 94, the energy detector 96 detects that the electronic cassette 24 is positioned within a feeding area of the power feeder 25, and sends a feeding area detection signal to the cassette controller 46.

Each of the LC resonators 84, 88, 94 has an LC resonance circuit comprising a coil and a capacitor. The power feeder 25 can contactlessly (wirelessly) supply electric power to the electronic cassette 24 according to the known power transmission technology which utilizes the resonance of the magnetic field M (magnetic resonance) from the LC resonator 84 to the LC resonator 88.

As shown in FIG. 5, the cassette controller 46 comprises an address signal generator 98, an image memory 100, an operation manager 102, a cassette ID memory 104, and a data manager 106. The address signal generator 98 supplies address signals to the address decoder 60 of the line scanning driver 58 of the radiation detector 40 and the address decoder 68 of the multiplexer 66 of the radiation detector 40. The image memory 100 stores radiographic image information detected by the radiation detector 40.

The operation manager 102 controls operation of the wireless power receiver 49 and the battery 44, and also controls overall operation of the electronic cassette 24. The operation manager 102 comprises a feeding-state determining unit 107, and an image-capturing-operation processing unit. The feeding-state determining unit 107 determines whether the wireless power receiver is supplying (charging) a battery with electricity or not (i.e., whether power-feeding is being performed or not). The image-capturing-operation processing unit performs a process for invalidating the image-capturing operation by the image capturing apparatus 22 if at least the feeding state determining unit 107 judges that power-feeding is being performed.

More specifically, the image-capturing-operation processing unit includes a signal generator 109 for generating an image-capturing inhibition signal and an image-capturing permission signal depending on a judgment result by the feeding-state determining unit 107, or for generating only an image-capturing permission signal.

The signal generator 109 may adopt a first type or a second type. In the first type, if the feeding-state determining unit 107 judges that power-feeding is being performed, the signal generator 109 generates the image-capturing inhibition signal for inhibiting the image-capturing of a patient by the image capturing apparatus 22, and if the feeding-state determining unit 107 judges that power-feeding is not performed, the signal generator 109 generates the image-capturing permission signal for permitting the image-capturing of the patient by the image capturing apparatus 22. That is, the first type signal generator 109 may include an image-capturing inhibition signal generator and an image-capturing permission signal generator. In the second type, if the feeding-state determining unit 107 judges that power-feeding is being performed, the signal generator 109 does not generate any signal, and if the feeding-state determining unit 107 judges that power-feeding is not performed, the signal generator 109 generates the image-capturing permission signal. That is, the second type signal generator 109 may include an image-capturing permission signal generator. The type is appropriately selected, for example, depending on the size of a radiographic image capturing system or the like.

Next, explanation will be made in a case where the first type signal generator is adopted. If the charging circuit 90 supplies the signal Sa indicating that power-feeding is being performed, the feeding-state determining unit 107 outputs, to the signal generator 109, a first signal indicating that power-feeding is being performed. At the time when the feeding-state determining unit 107 supplies the first signal, the signal generator 109 generates the image-capturing inhibition signal. Conversely, if the charging circuit 90 does not supply the signal Sa, the feeding-state determining unit 107 outputs, to the signal generator 109, a second signal indicating that power-feeding is not performed. At the time when the feeding-state determining unit 107 supplies the second signal, the signal generator 109 generates the image-capturing permission signal. As described above, the signal generator 109 generates an image-capturing inhibition signal and an image-capturing permission signal in response to a judgment result by the feeding-state determining unit 107. Thus, the signal generator 109 may be configured as a plurality of signal generators for generating the respective signals.

The image-capturing inhibition signal and the image-capturing permission signal which are generated by the signal generator 109 are transmitted to the console 28. When the console 28 receives these signals, the console 28 performs a control process for inhibiting (stopping) irradiation by the image capturing apparatus 22 and a control process for starting (resuming) irradiation by the image capturing apparatus 22. Alternatively, the electronic cassette 24 may directly transmit the image-capturing inhibition and permission signals to the image capturing apparatus 22, not through the console 28, and, for example, the radiation source controller 78 may perform the control processes for inhibiting and starting the image-capturing.

The cassette ID memory 104 stores cassette ID information for identifying the electronic cassette 24. The data manager 106 manages ID information (ID data) for identifying the power feeder 25 which feeds the electronic cassette 24 and a feeding area detection signal from the energy detector 96.

The transceiver 48 of the electronic cassette 24 receives a transmission request signal from the console 28 and the ID information of the power feeder 25 by way of wireless communications, and transmits the radiographic image information, the cassette ID information, a wireless feeding enable signal, the image-capturing inhibition signal, the image-capturing permission signal, etc. to the console 28.

The display device 26 comprises a receiver 110 for receiving the radiographic image information from the console 28, a display controller 112 for processing the received radiographic image information, and a display unit 114 for displaying the radiographic image information processed by the display controller 112.

The console 28 comprises a transceiver 116, an image capturing condition manager (image-capturing controller) 118, an image processor 120, an image memory 122, a patient information manager 124, a cassette information manager 126, and a power feeding information manager 128. The console 28 may be located outside of the operating room 12 insofar as it can reliably transmit and receive signals to and from the image capturing apparatus 22, the electronic cassette 24, the power feeder 25, and the display device 26.

The transceiver 116 of the console 28 transmits and receives necessary information including radiographic image information, and the image-capturing inhibition and permission signals to and from the image capturing apparatus 22, the electronic cassette 24, the power feeder 25, and the display device 26 by way of wireless communications. The image capturing condition manager 118 manages image capturing conditions required for the image capturing apparatus 22 to capture radiographic images, and also performs the control process for starting (resuming) the image capturing by the image capturing apparatus 22 and the control process for inhibiting the image capturing by the image capturing apparatus 22 based on the image capturing permission signal and the image capturing inhibition signal received from the signal generator 109. The image processor 120 processes radiographic image information transmitted from the electronic cassette 24. The image memory 122 stores the radiographic image information processed by the image processor 120. The patient information manager 124 manages patient information of the patient 14 whose images are to be captured. The cassette information manager 126 manages the wireless feeding enable signal and the cassette information including the cassette ID information transmitted from the electronic cassette 24. The power feeding information manager 128 manages the operation control of the power feeder 25 and ID information sent from the power feeder 25.

The image capturing conditions refer to conditions for determining a tube voltage, a tube current, an irradiation time, etc. required to apply radiation X at an appropriate dose to an area to be imaged of the patient 14. The image capturing conditions may include an area to be imaged of the patient 14, an image capturing method, etc., for example. The patient information refers to information for identifying the patient 14, such as the name, gender, patient ID number, etc. of the patient 14. Ordering information for instructing the image capturing system 10 to capture a radiation image, including the image capturing conditions and the patient information, can be set directly on the console 28 or can be supplied from an external source to the console 28 via the RIS 29. The cassette information includes the wireless feeding enable signal from the data manager 106 in addition to the cassette ID information for identifying the electronic cassette 24.

Next, explanation will be made in a case where the second type signal generator is adopted. If the charging circuit 90 does not supply the signal Sa indicating that power-feeding is being performed, the feeding-state determining unit 107 outputs, to the signal generator 109, the second signal indicating that power-feeding is not performed. At the time when the feeding-state determining unit 107 supplies the second signal, the signal generator 109 generates the image-capturing permission signal. Conversely, if the charging circuit 90 supplies the signal Sa, the feeding-state determining unit 107 outputs, to the signal generator 109, the first signal indicating that power-feeding is being performed. At the time when the feeding-state determining unit 107 supplies the first signal, the signal generator 109 stops generating of the image-capturing permission signal. That is, while the feeding-state determining unit 107 supplies the second signal, the signal generator 109 generates the image-capturing permission signal, and while the feeding-state determining unit 107 supplies the first signal, the signal generator 109 does not generate the image-capturing permission signal.

The image-capturing permission signal generated by the signal generator 109 is transmitted to the console 28. While the image-capturing permission signal is not supplied, the console 28 performs a control process for inhibiting (stopping) irradiation by the image capturing apparatus 22. On the other hand, while the image-capturing permission signal is supplied, the console 28 performs a control process for starting (resuming) irradiation by the image capturing apparatus 22. Alternatively, the electronic cassette 24 may directly transmit the image-capturing permission signal to the image capturing apparatus 22, not through the console 28, and, for example, the radiation source controller 78 may perform the control processes for inhibiting and starting the image-capturing.

The image capturing system 10 according to the embodiment is basically constructed as described above, and operation of the image capturing system 10 will be described below.

The image capturing system 10 is installed in the operating room 12 and used when radiographic images of the patient 14 are required by the surgeon 18 who is performing a surgical operation on the patient 14. Before radiographic images of the patient 14 are captured, patient information of the patient 14 to be imaged are registered in the patient information manager 124 of the console 28. If an area to be imaged of the patient 14 and an image capturing method have already been known, they are registered beforehand as image capturing conditions in the image capturing condition manager 118. After the above preparatory process is finished, the surgeon 18 performs a surgical operation on the patient 14.

Firstly, operation in the case of the first type signal generator 109 will be described with reference to FIG. 6.

Figure 6:
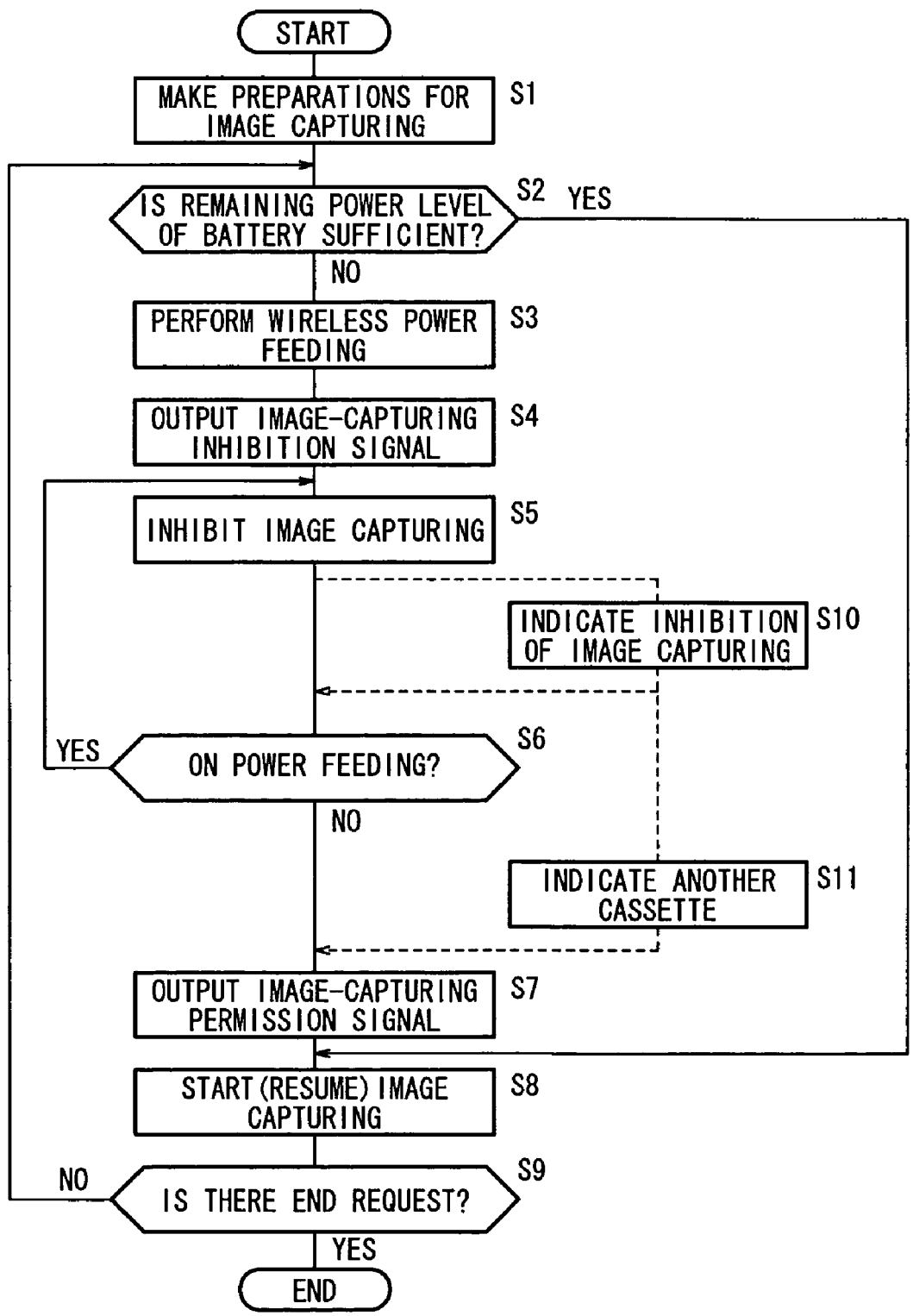
FIG. 6 is a flowchart of an image capturing sequence of the radiographic image capturing system shown in FIG. 4.

In step S1 shown in FIG. 6, the image capturing system prepares to capture radiographic images. For capturing radiographic images of the patient 14 during the surgical operation, the surgeon 18 or a radiological technician working on the image capturing system 10 places the electronic cassette 24 in a desired position between the patient 14 and the surgical table 16 with the irradiated surface 36 facing the image capturing apparatus 22.

At the same time that the console 28 starts to operate or when the surgeon 18 or the radiological technician turns on an operation start switch, not shown, the power feeder 25 is energized under given operating conditions (a low output operation mode). The electronic cassette 24 is now detected as being placed within the feeding area of the power feeder 25 by the detecting LC resonator 94 and the energy detector 96 of the wireless power receiver 49. Specifically, the energy detector 96 functions as a power feeding enable/disable detector for detecting whether the electronic cassette 24 is placed within the feeding area of the power feeder 25 or not. At this time, the power feeding controller 86 of the power feeder 25 operates in the low output operation mode for applying, from the LC resonator 84, a relatively weak magnetic field M which can be detected by the detecting LC resonator 94 and the energy detector 96 of the wireless power receiver 49. Therefore, the power consumption of the power feeder 25 is kept at a low level.

In the electronic cassette 24, the energy detector 96 supplies a feeding area detection signal to the data manager 106. In response to the feeding area detection signal, the data manager 106 receives the ID information of the power feeder 25 which is stored in the power feeding information manager 128 from the console 28, and transmits the wireless feeding enable signal to the cassette information manager 126 of the console 28.

The energy detector 96 also supplies the feeding area detection signal to the operation manager 102. In response to the feeding area detection signal, the operation manager 102 turns on the electronic cassette 24 to make it ready for use, thereby completing preparations for image capturing. Of course, the electronic cassette 24 may have, for example, on a side thereof, a power supply switch, not shown, which can be operated by the surgeon 18 or the radiological technician.

After the preparations for image capturing have been completed, the process goes to step S2, in which it is determined whether the remaining power level of the battery is sufficient or not. The cassette controller 46 or the cassette information manager 126 manages the remaining power level of the battery 44 to perform the above determination process. More specifically, when the image capturing system 10 captures an image according to certain image capturing conditions, the cassette controller 46 or the cassette information manager 126 compares the amount of electric power required for the image-capturing process with the present remaining power level of the battery 44, and thus judges whether the present remaining power level is enough for performing the image capturing process or not.

If the present remaining power level of the battery is not enough for performing the image capturing process, i.e., if it is judged that the battery 44 needs to be charged, then the process goes to step S3, in which the power feeder starts contactless power-feeding (wireless power-feeding). More specifically, the cassette information manager 126 of the console 28 sends a power feeding start signal to the power feeding controller 86 of the power feeder 25. Based on the power feeding start signal supplied from the console 28, the contactless (wireless) power-feeding is started with respect to the electronic cassette 24. The power feeder 25 now supplies electric power to the electronic cassette 24, i.e., charges the battery 44 of the electronic cassette 24 with a desired amount of electric power at a desired timing. If the remaining power level of the battery 44 runs low during the surgical operation, then the battery 44 may be charged while it is being kept in the given image capturing position. If the remaining power level of the battery 44 runs low during the preparations for image capturing, i.e., while the electronic cassette 24 is being placed in position, or before radiographic images start being captured, then the battery 44 can be charged in a contactless (wireless) fashion immediately before or after the surgical operation is started, so that the preparations for image capturing can be completed quickly.

For contactlessly (wirelessly) supplying electric power to the electronic cassette 24, the power feeder 25 may be energized to apply the magnetic field M from the LC resonator 84 to the electronic cassette 24 under given operating conditions for a stronger level than in the low output operation mode (high output operation mode, power feeding operation mode). In the electronic cassette 24, the energy received by the detecting LC resonator 94 as well as the energy received by the LC resonator 88, may be used to charge the battery 44 through the charging circuit 90, for thereby quickly charging the battery 44.

The image capturing system 10 allows the console 28 to confirm the ID information of the power feeder 25 that is associated with the electronic cassette 24. Accordingly, even if the image capturing system 10 includes a plurality of power feeders that are selectively usable, the electronic cassette 24 can be appropriately and selectively supplied with electric power from a desired selected one of the power feeders based on the ID information confirmed by the console 28. As a result, wasteful power consumption and erroneous operation can be avoided.

When the power feeder starts contactless (wireless) power-feeding, the charging circuit 90 of the electronic cassette 24 outputs the signal Sa indicating that power-feeding is being performed, in step S4. Then, the feeding-state determining unit 107 outputs the first signal, and the signal generator 109 outputs the image-capturing inhibition signal. The image-capturing inhibition signal is sent to the console 28. In case that the console 28 receives the image-capturing inhibition signal, the console 28 performs a control process for inhibiting the image-capturing by the image capturing apparatus 22, under control of, for example, the image capturing condition manager 118 (step S5). Alternatively, the electronic cassette 24 may send the image-capturing inhibition signal directly to the image capturing apparatus 22, not through the console 28, and then the radiation source controller 78 of the image capturing apparatus 22 or the cassette controller 46 of the electronic cassette 24 may perform the control process for inhibiting the image-capturing.

Accordingly, the radiographic image capturing process by the image capturing apparatus 22 is avoided during the power-feeding period. Thus, the captured radiographic image is prevented from being adversely affected by noise due to voltage fluctuation of the battery 44, magnetic field M and the like.

If the control for inhibiting the radiographic image capturing process by the image capturing apparatus 22 is being performed after the console 28 has received the image-capturing inhibition signal until conversion of electric power by the charging circuit 90 of the electronic cassette 24 is finished, or more preferably until wireless communication for power-feeding by the power feeder 25 is stopped, the radiation detector 40 can detect radiation X highly accurately. In the above example, when conversion of electric power by the charging circuit 90 of the electronic cassette 24 is finished, the feeding-state determining unit 107 outputs the second signal indicating that power-feeding is not performed, and as a result, the signal generator 109 generates the image-capturing permission signal. Alternatively, the time period required for capturing and displaying radiographic images may be estimated in advance, and the console 28 may keep inhibiting the image-capturing by the image capturing apparatus 22 during a given time based on the estimated time period after reception of the image-capturing inhibition signal.

Thereafter, in step S6, it is determined whether power-feeding is being performed or not at present. This determination process is performed based on whether power conversion by the charging circuit 90 of the electronic cassette 24 is finished or not, or whether wireless communication for power-feeding by the power feeder 25 is stopped or not.

When power conversion by the charging circuit 90 of the electronic cassette 24 is not finished or when wireless communication for power-feeding by the power feeder 25 is not stopped, it is judged that power-feeding is being performed. Then, the control for inhibiting the image-capturing in step S5 is maintained.

On the other hand, when the electric power level of the battery 44 reaches the amount of electric power required for the image capturing process by battery charge and then power conversion by the charging circuit 90 of the electronic cassette 24 is finished or when the electric power level reaches the amount of electric power required for the image capturing process and then wireless communication for power-feeding by the power feeder 25 is stopped, it is judged that power-feeding is not performed. Then, the process goes to step S7, in which the signal generator 109 generates the image-capturing permission signal. Subsequently, the process goes to step S8. In step S8, the surgeon 18 or the radiological technician moves the image capturing apparatus 22 to a position facing the electronic cassette 24, and thereafter operates the image capturing switch 72 to capture radiographic images.

When the surgeon 18 or the radiological technician operates the image capturing switch 72, the radiation source controller 78 of the image capturing apparatus 22 sends a request to the console 28 for sending the image capturing conditions. Based on the received request, the console 28 sends the image capturing conditions for an area to be imaged of the patient 14 which are registered in the image capturing condition manager 118, to the image capturing apparatus 22. In case that the radiation source controller 78 receives the image capturing conditions, it controls the radiation source 74 to apply radiation X at a given dose to the patient 14 according to the image capturing conditions. The image capturing conditions may be sent in advance from the console 28 to a memory, not shown, in the radiation source controller 78.

The radiation X which has passed through the patient 14 is applied to the grid 38, which removes scattered rays of the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 3). The stored electric charges (signal charges), which represent radiographic image information of the patient 14, are read from the storage capacitors 53 according to address signals which are supplied from the address signal generator 98 of the cassette controller 46 to the line scanning driver 58 and the multiplexer 66.

Specifically, in response to the address signal supplied from the address signal generator 98, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 98, the address decoder 68 of the multiplexer 66 outputs a selection signal that successively turns the switches SW2 on in order to switch between the signal lines 56, for thereby reading the electric charges stored in the storage capacitors 53 of the pixels 50 connected to the selected gate line 54, through the signal lines 56.

The electric charges read from the storage capacitors 53 of the pixels 50 connected to the selected gate line 54 are amplified by the respective amplifiers 62, sampled by the sample and hold circuits 64, and supplied to the multiplexer 66. Based on the supplied electric charges, the multiplexer 66 generates and supplies a radiographic image signal to the A/D converter 70, which converts the radiographic image signal into a digital signal. The digital signal which represents the radiographic image information is stored in the image memory 100 of the cassette controller 46.

Similarly, the address decoder 60 of the line scanning driver 58 successively turns on the switches SW1 to switch between the gate lines 54 according to the address signal supplied from the address signal generator 98. The electric charges stored in the storage capacitors 53 of the pixels 50 connected to the successively selected gate lines 54 are read through the signal lines 56, and processed by the multiplexer 66 and the A/D converter 70 into digital signals (step S7), which are stored in the image memory 100 of the cassette controller 46.

The radiographic image information represented by the digital signals stored in the image memory 100 is transmitted to the console 28 by way of wireless communications. The radiographic image information transmitted to the console 28 is received by the transceiver 116, processed by the image processor 120, and then stored in the image memory 122 in association with the patient information of the patient 14 registered in the patient information manager 124.

The radiographic image information processed by the image processor 120 is transmitted from the console 28 to the display device 26. In the display device 26, the receiver 110 receives the radiographic image information, and the display controller 112 controls the display unit 114 to display a radiographic image based on the radiation image information. The surgeon 18 can perform the surgical operation on the patient 14 while visually confirming the radiographic image displayed on the display unit 114.

Thereafter, in step S9, it is determined whether or not there is an end request (power discontinuity request, maintenance request, etc.) with respect to the image capturing system 10. If there is not an end request, the process returns to step S2 and the above sequence is performed again. If there is an end request, the process sequence in the image capturing system 10 is finished.

Next, operation in the case of the second type signal generator 109 will be described with reference to FIG. 7. Incidentally, the same processes as in the above case of the first type signal generator 109 are not described below.

Figure 7:
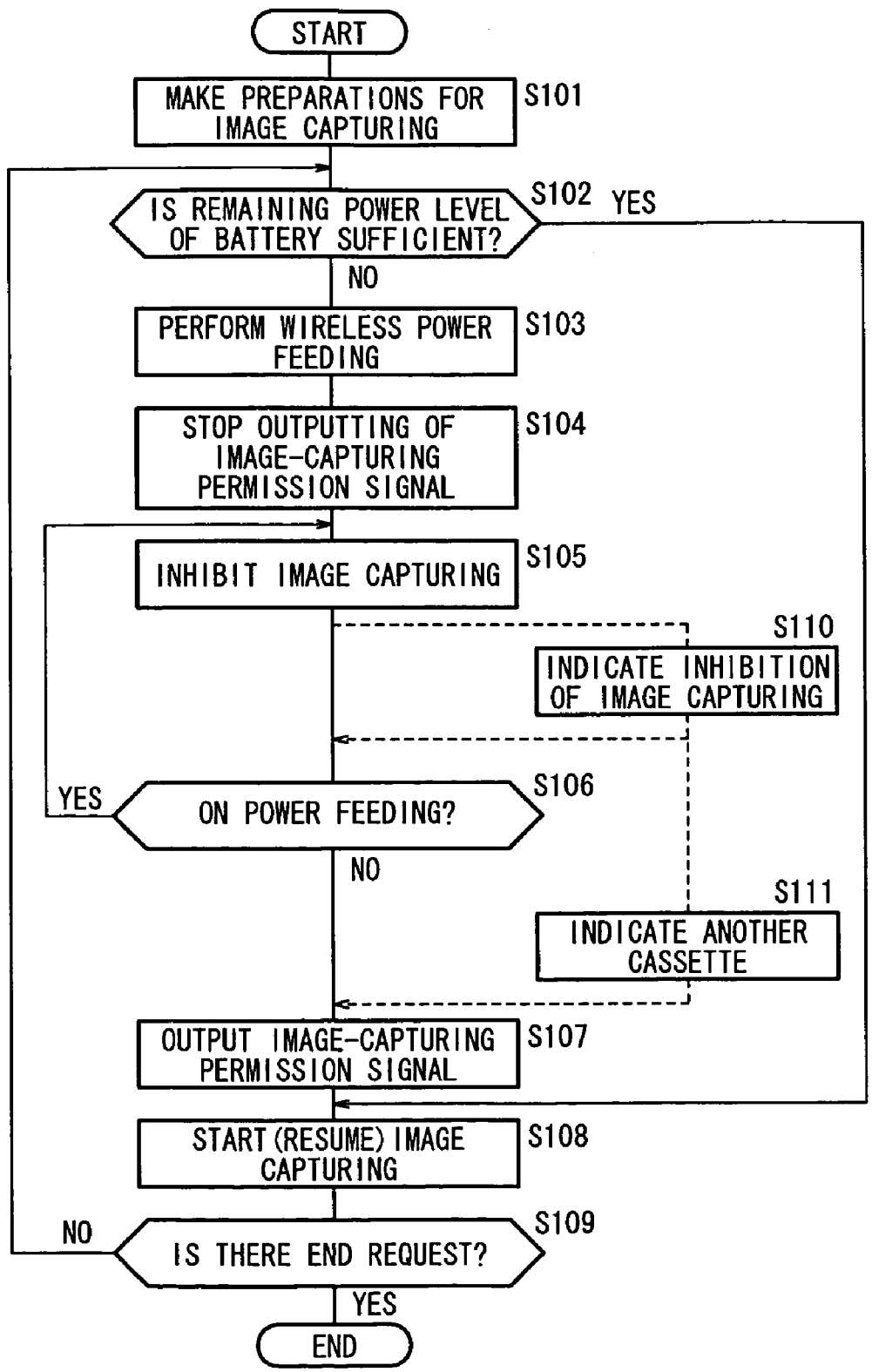
FIG. 7 is a flowchart of another image capturing sequence of the radiographic image capturing system shown in FIG. 4.

In step S101 shown in FIG. 7, the image capturing system prepares to capture radiographic images. After the preparations for image capturing have been completed, the process goes to step S102, in which it is determined whether the remaining power level of the battery is sufficient or not. In this case also, the cassette controller 46 or the cassette information manager 126 compares the amount of electric power required for performing the image-capturing process according to the image capturing conditions with the present remaining power level of the battery 44, and then judges whether the present remaining power level is enough for performing the image capturing process or not. If it is judged that the battery 44 needs to be charged, then the process goes to step S103, in which the power feeder starts contactless power-feeding (wireless power-feeding). When the power feeder starts contactless (wireless) power-feeding, the charging circuit 90 of the electronic cassette 24 outputs the signal Sa indicating that power-feeding is being performed, in step S104. Then, the feeding-state determining unit 107 outputs the first signal. At this time, if the signal generator 109 is outputting the image-capturing permission signal, the signal generator 109 stops outputting of the image-capturing permission signal. That is, the console 28 is not supplied with the image-capturing permission signal. Accordingly, the console 28 performs a control process for inhibiting the image-capturing by the image capturing apparatus 22, under control of, for example, the image capturing condition manager 118 (step S105). Alternatively, if the electronic cassette 24 may send the image-capturing permission signal directly to the image capturing apparatus 22, not through the console 28, then the radiation source controller 78 of the image capturing apparatus 22 or the cassette controller 46 of the electronic cassette 24 may perform the control process for inhibiting the image-capturing, based on stoppage of outputting of the image-capturing permission signal in step S104.

Owing thereto, the radiographic image capturing process by the image capturing apparatus 22 is avoided during the power-feeding period. Thus, the captured radiographic image is prevented from being adversely affected by noise due to voltage fluctuation of the battery 44, magnetic field M and the like.

Thereafter, in step S106, it is determined whether power-feeding is being performed at present or not. When power conversion by the charging circuit 90 of the electronic cassette 24 is not finished or when wireless communication for power-feeding by the power feeder 25 is not stopped, it is judged that power-feeding is being performed. Then, the control for inhibiting the image-capturing in step S105 is maintained.

On the other hand, when the electric power level of the battery 44 reaches, by the battery charge, the amount of electric power enough for performing the image capturing process and then power conversion by the charging circuit 90 of the electronic cassette 24 is finished or when the electric power level of the battery 44 reaches the amount of electric power enough for performing the image capturing process and then wireless communication for power-feeding by the power feeder 25 is stopped, it is judged that power-feeding is not performed. Then, the process goes to step S107, in which the signal generator 109 outputs the image-capturing permission signal.

Subsequently, the process goes to step S108. In step S108, the surgeon 18 or the radiological technician moves the image capturing apparatus 22 to a position facing the electronic cassette 24, and thereafter operates the image capturing switch 72 to capture radiographic images.

Thereafter, in step S109, it is determined whether or not there is an end request (power discontinuity request, maintenance request, etc.) with respect to the image capturing system 10. If there is not an end request, the process returns to step S102 and the above sequence is performed again. If there is an end request, the process sequence in the image capturing system 10 is finished.

In the image capturing system 10, even if the remaining power level of the battery 44 of the electronic cassette 24 runs low due to a plurality of radiographic images captured during the surgical operation, since the image capturing system 10 has the power feeder 25 which is capable of feeding the electronic cassette 24 contactlessly (wirelessly), the battery 44 of the electronic cassette 24 can be charged with the electronic cassette 24 being kept in the image capturing position.

However, if the contactless (wireless) feeding is performed while a radiographic image is being captured, the voltage supplied from the battery 44 to the radiation detector 40 tends to become unstable and fluctuate greatly, and noise caused by the magnetic field M applied from the power feeder 25 may adversely affect the radiation detector 40. In this case, the captured radiographic image is liable to contain the noise and the image capturing system 10 is highly likely to fail to acquire radiographic images of high quality.

The image capturing system 10 according to the present embodiment is arranged to overcome the above difficulties as follows: The image capturing system 10 includes the feeding-state determining unit 107, and the signal generator 109, which operate to permit and inhibit the radiographic image capturing by the image capturing apparatus 22 based on whether power-feeding is being performed or not.

As described above, even though the image-capturing inhibition control is performed during the power-feeding, the image capturing system 10 can quickly cause the image capturing apparatus to capture radiographic images after the power-feeding has been finished. This is particularly effective when the next image-capturing process needs to be performed immediately after recharging of the battery 44 in the case where the remaining power level thereof has been greatly reduced during the image-capturing process.

The image capturing system 10 may be configured to charge the battery 44 under the control of the console 28 at desired times other than when radiographic images are captured.

As described above, with the image capturing system 10 according to the present embodiment, even though the electronic cassette 24 is placed in a desired image capturing position with respect to the patient 14, the power feeder 25 can easily supply electronic power to the electronic cassette 24. Even if the battery 44 of the electronic cassette 24 needs to be charged during the surgical operation, the battery 44 can be charged without the need for moving the electronic cassette 24. Accordingly, the electronic cassette 24 and the image capturing system 10 can be handled with ease as a whole. Furthermore, the process of capturing a radiographic image and the surgical operation are effectively prevented from being interrupted and prolonged due to a low remaining power level of the battery 44 of the electronic cassette 24.

The image capturing system 10 (electronic cassette 24) has the feeding-state determining unit 107 and the signal generator 109, and the image-capturing process of radiation X is prevented from being performed during the power-feeding by the power feeder 25. The radiographic image is prevented from being adversely affected by noise caused by the contactless (wireless) power feeding from the power feeder 25. Therefore, it is possible to acquire radiographic images of high quality. In this case, in order to more reliably prevent the image capturing apparatus 22 from capturing radiographic images during the power-feeding period, the display unit 114 of the display device 26 may display "ON POWER-FEEDING" or "ON IMAGE-CAPTURING". Thereby, the surgeon 18 or the like can grasp the current situation more reliably and easily, and thus, radiographic image-capturing and contactless (wireless) power feeding can be performed more smoothly.

Further, when it is judged that power-feeding is not performed (end of power-feeding), the feeding-state determining unit 107 and the signal generator 109 may generate the image-capturing permission signal for permitting starting (resuming) of image-capturing. Therefore, even if the remaining power level of the battery 44 is greatly lowered by an image capturing process, the battery 44 can quickly be charged after the image capturing process and made ready for a next image capturing process.

When the electronic cassette 24 is placed within the feeding area of the power feeder 25, the electronic cassette 24 and the power feeder 25 automatically exchanges information with each other through the console 28, and the electronic cassette 24 is automatically brought into a state capable of capturing a radiographic image. Consequently, the electronic cassette 24 is not required to have a manual power supply switch, and the surgeon 18 or the radiological technician is prevented from making a mistake not to capture a radiographic image by forgetting to operating such a manual power supply switch. Accordingly, the electronic cassette 24 and the image capturing system 10 can be handled with greater ease as a whole.

If the energy detector 96 of the electronic cassette 24 does not detect the desired magnetic field M, then the data manager 106 may send a wireless feeding disable signal, for example, to the cassette information manager 126, from which the wireless feeding disable signal is sent to the display device 26 for indicating to the surgeon 18 or the radiological technician that it is not possible to supply electric power from the power feeder 25 to the electronic cassette 24, on the display unit 114.

In the above examples, processes during an operation are mainly described. However, the above processes are applicable to a routine health checkup, a radiographic image capturing process while a patient is being transferred by vehicle, and other cases.

In step S10, S110 after step S5, S105 shown in FIGS. 6, 7, the display unit 114 may inform the surgeon 18 that the image capturing process by the image capturing apparatus 22 is inhibited at present. Accordingly, the surgeon 18 can grasp that operation of the image capturing switch 72 is invalid and the radiation source 74 does not emit radiation X.

In this case, after step S10, S110, the process goes to step S6, S106. If it is judged in step S6, S106 that power-feeding is being performed (YES in step S6, S106), then the process returns to step S5, S105, in which the display unit 114 may notify the surgeon 18 of the remaining electric power level of the battery 44 that is being charged and the remaining charging time before completion of the battery charge (remaining charging time before the electric power level of the battery 44 reaches the amount of electric power enough for performing the image capturing process). Owing thereto, the surgeon 18 can grasp clearly the present remaining electric power level of the battery and the remaining charging time before completion of the battery charge. Thus, using the remaining time effectively, the surgeon 18 can perform another process, thereby performing an operation, etc., efficiently.

Alternatively, after step S10, S110, the process goes to step S11, S111, the display unit 114 may inform (notify) the surgeon 18 that there is another fully-charged electronic cassette 24 in the operation room 12, instead of the electronic cassette 24 that is being charged at present. If the surgeon 18 can not wait for completion of charging the electronic cassette 24 for some reason, the surgeon 18 visually confirm the information displayed on the display unit 114, and then can immediately start the image capturing process using the other electronic cassette 24. Thus, a radiographic image of the patient 14 can be obtained swiftly.

In this case, in step S7, S107 after step S11, S111, the signal generator 109 of the other electronic cassette 24 generates the image-capturing permission signal. In the subsequent step S8, S108, if the surgeon 18 operates the image capturing switch 72, a radiographic image can be captured using the other electronic cassette 24.

Figure 8:
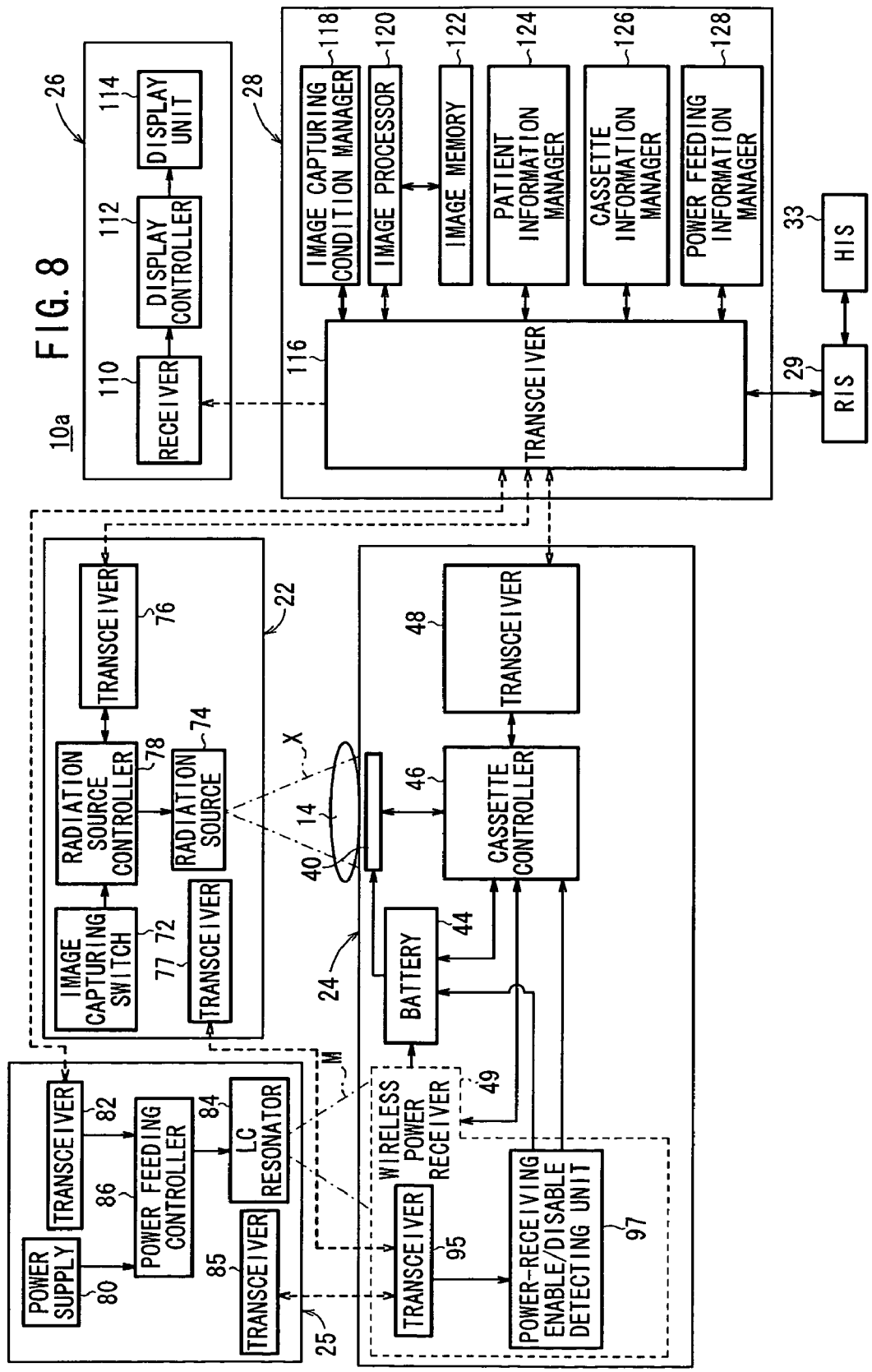
FIG. 8 is a block diagram of a radiographic image capturing system according to a first modification of the radiographic image capturing system shown in FIG. 4.

As shown in FIG. 8, the image capturing system 10 according to the present embodiment may be configured as a radiographic image capturing system 10*a* according to a first modification in which a transceiver 85 and a transceiver 77 are provided in the power feeder 25 and the image capturing apparatus 22, respectively, and a transceiver 95 and a power-receiving enable/disable detecting unit 97, instead of the detecting LC resonator 94 and the energy detector 96, are provided in the electronic cassette 24.

The image capturing system 10 shown in FIG. 4 uses the detecting LC resonator 94 and the energy detector 96 as the power-receiving enable/disable detecting unit for detecting whether or not the electronic cassette 24 is placed within the power-feeding area of the power feeder 25, i.e., whether or not the electronic cassette 24 can receive electric power from the power feeder 25.

On the other hand, in the image capturing system 10*a* shown in FIG. 8, signals indicating whether or not the electronic cassette 24 is placed within the feeding area of the power feeder 25 can be sent and received using communication between the transceiver 85 of the power feeder 25 and the transceiver 95 of the wireless power receiver 49. Wireless communication between the transceiver 85 and the transceiver 95 may preferably use a directional wireless communication which is capable of not affecting other wireless communications by limiting the communication area. Also, instead of the transceivers 85, 95, an LED (light emitting device) and a light-receiving device may be used to perform the similar detection.

In the image capturing system 10*a*, using wireless communication between the transceiver 95 of the wireless power receiver 49 and the transceiver 77 of the image capturing apparatus 22, the image capturing apparatus 22 can send the image-capturing start signal to the electronic cassette 24 just before starting of image-capturing. In this case, in case that the electronic cassette 24 receives the image-capturing start signal and the feeding-state determining unit 107 judges that power-feeding is being performed, the image-capturing inhibition signal from the first type signal generator 109 can be transmitted directly to the image capturing apparatus 22 by the transceiver 95 of the wireless power receiver 49 and the transceiver 77 of the image capturing apparatus 22, not through the console 28. Accordingly, radiographic image capturing during the power-feeding period is prevented more reliably. The image-capturing start control based on the image-capturing permission signal is performed similarly. Also, in the case of the second type signal generator 109, the image-capturing inhibition control based on stoppage of outputting of the image-capturing permission signal and the image-capturing start control based on outputting of the image-capturing permission signal are performed similarly.

Figure 9:
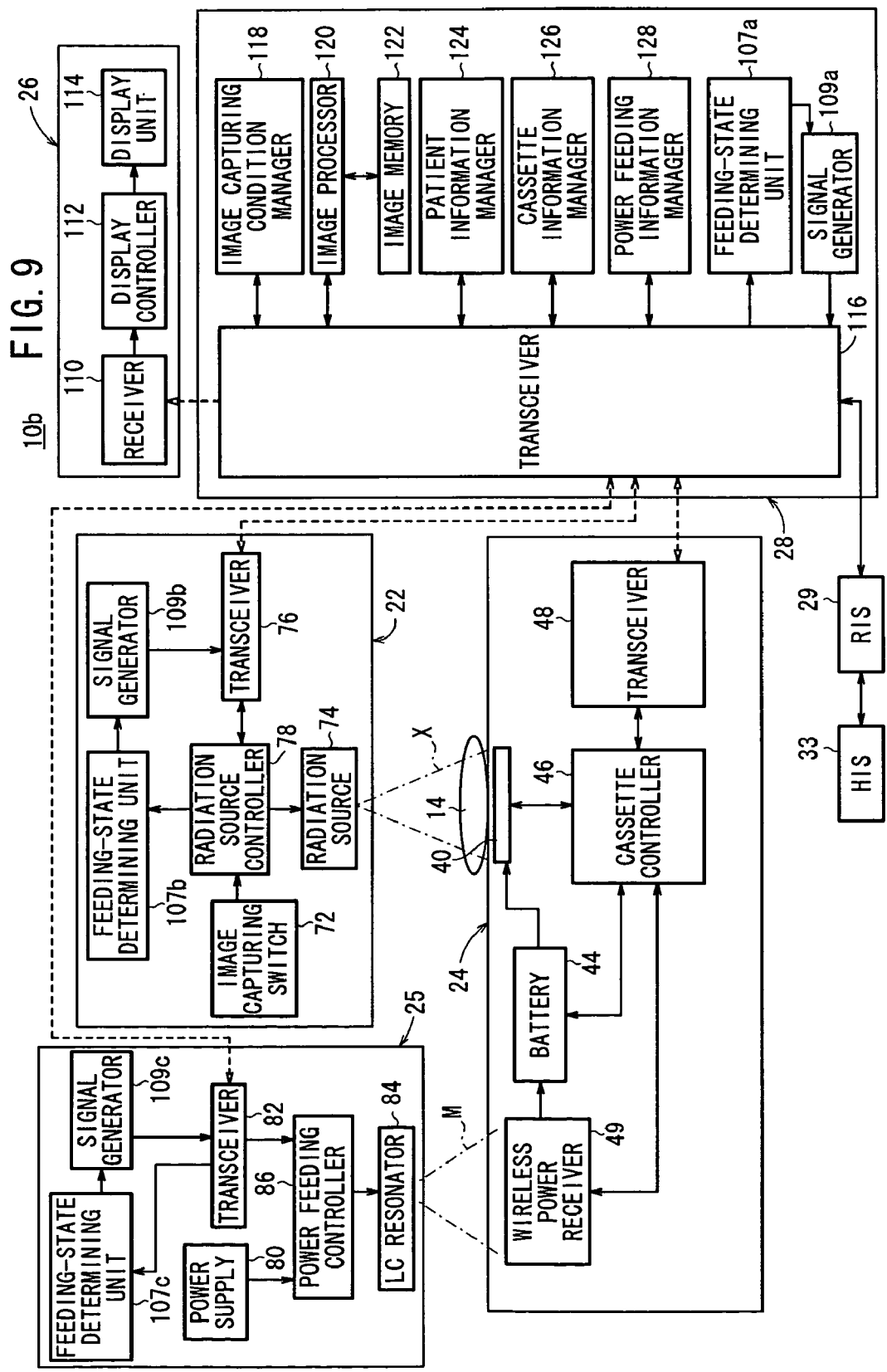
FIG. 9 is a block diagram of a radiographic image capturing system according to a second modification of the radiographic image capturing system shown in FIG. 4.

FIG. 9 is a block diagram of a radiographic image capturing system 10*b* according to a second modification of the radiographic image capturing system 10 shown in FIG. 4.

In the radiographic image capturing systems 10 described above, the feeding-state determining unit 107 and the signal generator 109, for controlling the inhibition of the image-capturing by the image capturing apparatus 22, are incorporated in the electronic cassette 24. In the radiographic image capturing system 10*b*, a feeding-state determining unit 107*a*, and a first type signal generator (or a second type signal generator) 109*a* are incorporated in the console 28, and control for inhibition of image-capturing during the power-feeding period and control for starting of image-capturing during the non-power-feeding period are performed.

In the radiographic image capturing system 10b, when a feeding start signal has been output from the cassette information manager, the feeding-state determining unit 107a judges that power-feeding is being performed, and on the basis of the judgment, the signal generator 109a sends the image-capturing inhibition signal (or stops outputting of the image-capturing permission signal), for thereby performing the control for inhibition of the image-capturing during the power-feeding period in the same manner as the image capturing system 10. The feeding-state determining unit 107 and the signal generator 109 that are incorporated in the electronic cassette 24 may be disabled under the control of the console 28. Alternatively, the radiographic image capturing system 10b may employ a simplified electronic cassette which is free of the feeding-state determining unit 107 and the signal generator 109.

As shown in FIG. 9, a feeding-state determining unit 107b and a first type signal generator (or a second type signal generator) 109b may be provided in the image capturing apparatus 22, in addition to or instead of the feeding-state determining unit 107a and the signal generator 109a, and a feeding-state determining unit 107c and a first type signal generator (or a second type signal generator) 109c may be provided in the power feeder 25. In other words, a feeding-state determining unit and a signal generator may be provided in at least one of the console 28, the image capturing apparatus 22, the power feeder 25 and the electronic cassette 24, thereby allowing the radiographic image capturing system 10b to perform the image-capturing inhibition control and the image-capturing start control (image-capturing stand-by control) in the same manner as the radiographic image capturing systems 10. In this case, the radiographic image capturing system 10b may include another dedicated console or the like. If a feeding-state determining unit and a signal generator are provided in each of a plurality of apparatus, then the feeding-state determining unit and the signal generator provided in any one of the apparatus may selectively be used under the control of the console 28, for example, whereas the functions of the feeding-state determining units and the signal generators provided in the other apparatus may be disabled.

Since the electronic cassette 24 incorporates the feeding-state determining unit 107 and the signal generator 109 (see FIG. 5), the control functions for inhibition of image-capturing and for starting of image-capturing (image-capturing stand-by control) can easily be added to an existing radiographic image capturing system simply by slightly modifying the control program of the console 28, advantageously.

The cassette controller 46 of the electronic cassette 24, the feeding information manager 128 of the console 28, the source controller 78 of the image capturing apparatus 22 and the feeding controller 86 of the power feeder 25 serve as an image-capturing inhibition controller (image-capturing start controller) which receives an image-capturing inhibition signal (image-capturing permission signal) transmitted from the first type signal generators 109, 109a, 109b, 109c, and controls the image capturing apparatus 22 to inhibit (start) radiographic image capturing by the image capturing apparatus 22. Alternatively, the cassette controller 46 of the electronic cassette 24, the feeding information manager 128 of the console 28, the source controller 78 of the image capturing apparatus 22 and the feeding controller 86 of the power feeder 25 serve as an image-capturing inhibition controller (image-capturing start controller) which controls the image capturing apparatus 22 to inhibit (start) radiographic image capturing by the image capturing apparatus based on whether the second type signal generator 109, 109a to 109c supplies the image-capturing permission signal or not. Thus, as in the case of the above feeding-state determining unit and signal generator, the image-capturing inhibition controller and the image-capturing start controller may be provided in at least one apparatus, and in other word, either one of the cassette controller 46, the feeding information manager 128 and the like may serve as the image-capturing inhibition controller and the image-capturing start controller.

With the radiographic image capturing systems 10, 10a, 10b, radiographic images used in a surgical operation are displayed by the display device 26. However, the radiographic image capturing systems 10, 10a, 10b may be used to capture ordinary radiographic images in applications other than surgical operations. Similarly, the electronic cassette 24 is not limited to use in the operating room 12, but may be used in medical examinations or used by doctors when going the rounds in hospitals, for example.

As described in the above explanations of the present embodiment, the power feeder 25 may be of any type insofar as it can supply electric power contactlessly (wirelessly) to the electronic cassette 24. For example, the power feeder 25 may comprise components made of a dielectric material for utilizing an electric field (electric field resonance) rather than the magnetic field (magnetic resonance), rather than the LC resonators 84, 88 and the detecting LC resonators 94, and hence may be other than the resonant wireless power feeder. Stated otherwise, the electric energy supplied from the power feeder 25 to the electronic cassette 24 may be optical energy, thermal energy, or other types of energy.

In the radiographic image capturing systems 10, 10a, 10b, the radiation detector 40 housed in the electronic cassette 24 directly converts the dose of the applied radiation X into an electric signal with the photoelectric conversion layer 51. However, the radiographic image capturing systems may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiographic image capturing systems may employ a light-conversion type radiation detector for acquiring radiographic image information. The light-conversion type radiation detector operates as follows: When radiation is applied to a matrix of solid-state detecting devices, the solid-state detecting devices store an electrostatic latent image depending on the dose of the applied radiation. For reading the stored electrostatic latent image, reading light is applied to the radiation detector, and the generated electric current values are acquired as radiation image information. When erasing light is applied to the radiation detector, radiographic image information representing a residual electrostatic latent image is erased from the radiation detector, which can thus be reused (see Japanese Laid-Open Patent Publication No. 2000-105297).

Signals may be sent and received between the image capturing apparatus 22, the power feeder 25, the display device 26, and the console 28 by way of wired communications.

Wireless communications between the electronic cassette 24 and external devices may be optical wireless communications based on infrared rays rather than ordinary radio-wave communications.

Figure 10:
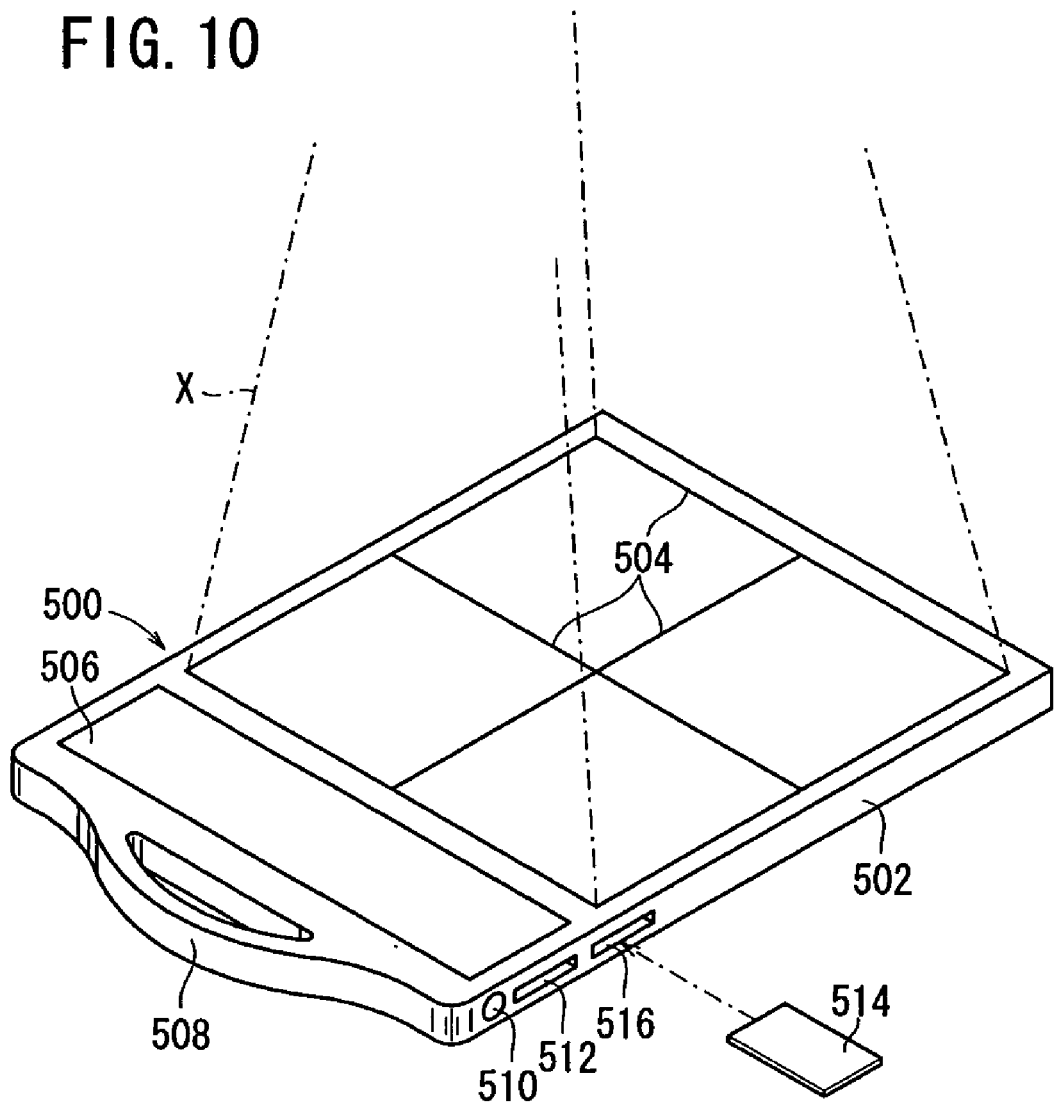
FIG. 10 is a perspective view of another electronic cassette.

FIG. 10 shows in perspective an electronic cassette 500 according to a modification of the electronic cassette 24.

As shown in FIG. 10, the electronic cassette 500 has guide lines 504 drawn on the irradiated surface of a casing 502 as a reference mark for an image capturing area and an image capturing position. Using the guide lines 504, the subject to be imaged, such as the patient 14, can be positioned with respect to the electronic cassette 500 and the range in which the radiation X is to be applied to the electronic cassette 500 can be determined, for thereby recording radiographic image information in an appropriate image capturing area of the electronic cassette 500.

The electronic cassette 500 also has a display unit 506 outside of the image capturing area thereof for displaying various items of information about the electronic cassette 500. Specifically, the display unit 506 displays ID information of the patient 14, whose radiation image is recorded in the electronic cassette 500, the number of times that the electronic cassette 500 has been used, an accumulated exposed dose, the charged state (remaining power level) of the battery 44 housed in the electronic cassette 500, image capturing conditions for radiographic image information, and a positioning image representing the patient 14 positioned with respect to the electronic cassette 500, etc. The radiological technician can confirm the patient 14 based on the ID information displayed on the display unit 506, also confirm in advance that the electronic cassette 500 is in a usable state, position the desired area to be imaged of the patient 14 with respect to the electronic cassette 500 based on the displayed positioning image, and capture optimum radiographic image information in the electronic cassette 500.

The electronic cassette 500 includes a handle 508 to be gripped by the user in order to handle and carry the cassette 500 with ease.

The cassette 500 also preferably has an input terminal 510 for connection to an AC adapter, a USB (Universal Serial Bus) terminal 512, and a card slot 516 for receiving a memory card 514, all provided on a side wall of the casing of the electronic cassette 500.

When the charging function of the battery 44 housed in the electronic cassette 500 is low or when there is not enough time to charge the battery 44, an AC adapter is connected to the input terminal 510 to supply electric power from an external source for thereby making the electronic cassette 500 immediately operable.

The USB terminal 512 or the card slot 516 can be used when the electronic cassette 500 is unable to send and receive information to and from an external device such as the console 28 or the like by way of wireless communications. Specifically, when a USB cable connected to the external device is connected to the USB terminal 512, the cassette 500 can send and receive information to and from the external device by way of wired communications through the USB terminal 512 and the USB cable. Alternatively, the memory card 514 is inserted into the card slot 516 and necessary information from the cassette 500 is recorded into the memory card 514. Thereafter, the memory card 514 is disconnected from the card slot 516 and then connected to the external device to send the information to the external device.

Figure 11:
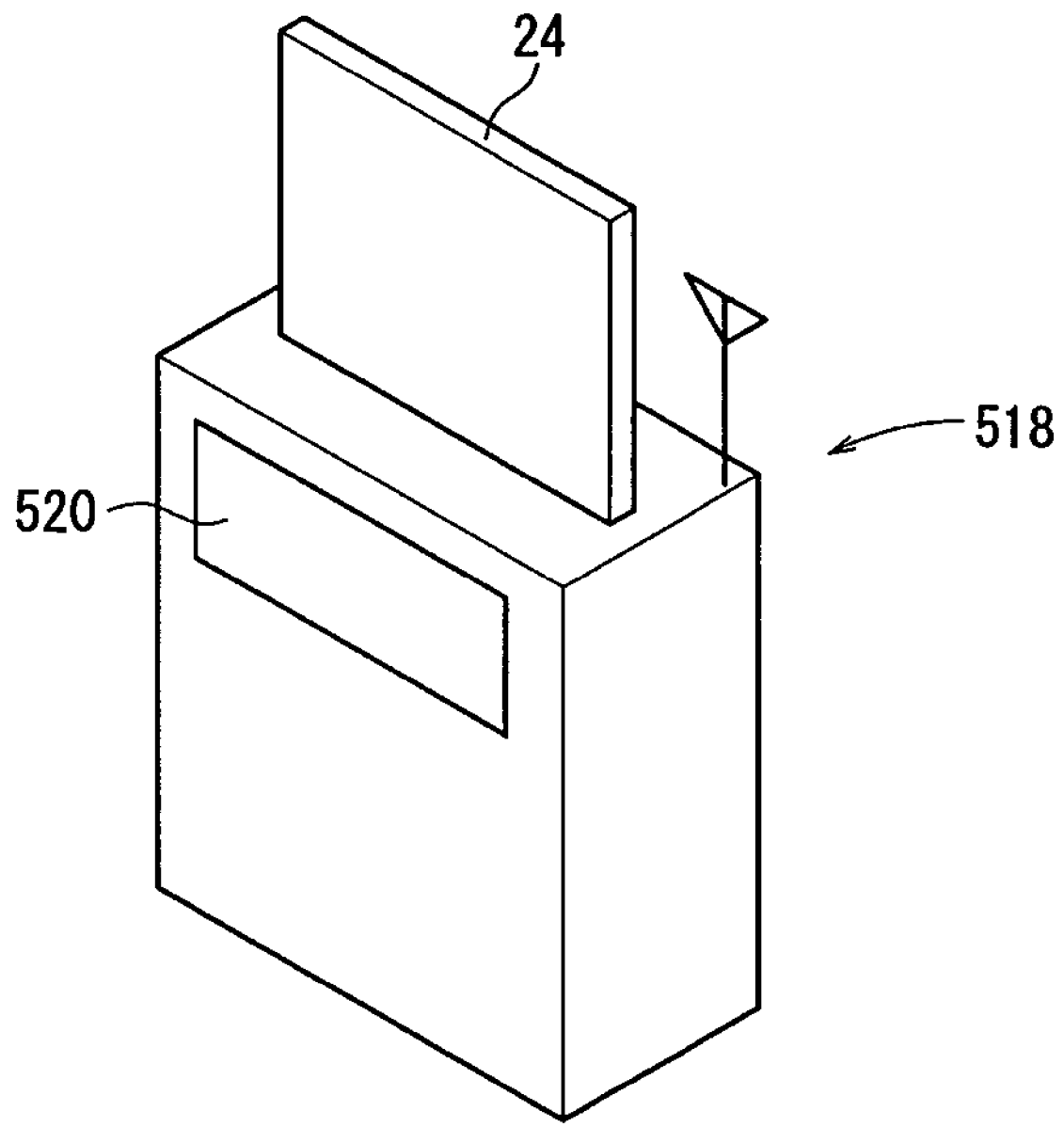
FIG. 11 is a perspective view of a cradle for charging a battery in the electronic cassette.

FIG. 11 shows a cradle 518 for receiving the electronic cassette 24 and charging the battery 44 housed in the electronic cassette 24. The cradle 518 should preferably be positioned in the operating room 12 or a desired location in the hospital. The cradle 518 may not only be able to charge the battery 44 with a contactless power feeder, not shown, similar to the above power feeder 25, but also have a wireless or wired communication function to send and receive necessary information to and from an external device, such as the RIS 29, the HIS 33, the console 28, or the like. The information that is sent and received may include radiation image information recorded in the electronic cassette 24 loaded in the cradle 518.

The cradle 518 has a display unit 520 for displaying the charged state of the battery 44 housed in the electronic cassette 24 and necessary information including radiation image, information acquired from the electronic cassette 24.

A plurality of cradles 518 may be connected to a network, and charged states of the batteries 44 housed in the electronic cassettes 24 loaded in the respective cradles 518 may be retrieved through the network, so that the user can confirm the locations of any electronic cassettes 24 whose batteries 44 are sufficiently charged, based on the retrieved charged states of the batteries 44.

Figure 12:
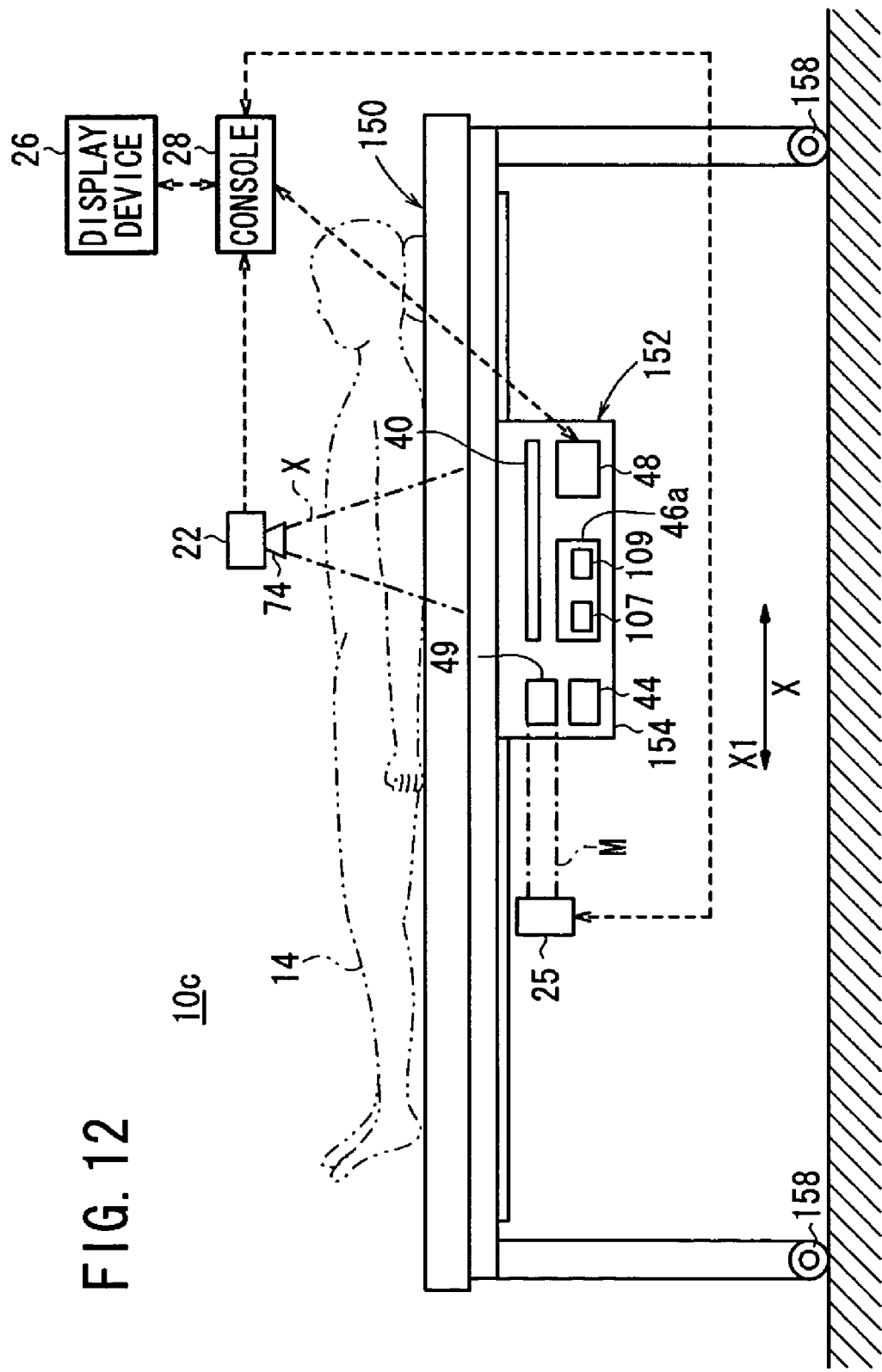
FIG. 12 is a side elevational view, partly in block form, of a radiographic image capturing system according to a third modification of the radiographic image capturing system shown in FIG. 4.

FIG. 12 is a side elevational view, partly in block form, of a radiographic image capturing system 10c according to a third modification of the radiographic image capturing system 10 shown in FIG. 4.

The radiographic image capturing systems 10, 10a, 10b employ the electronic cassette 24 as a radiation detecting apparatus for detecting the applied radiation X and acquiring radiographic image information. The radiographic image capturing system 10c shown in FIG. 12 employs, instead of the electronic cassette 24, a radiation detecting apparatus 152 incorporated in an image capturing table 150 for the patient 14 to lie thereon, for capturing a radiographic image of the patient 14 while the patient 14 is lying on the image capturing table 150.

The radiation detecting apparatus 152 is substantially the same in construction as the electronic cassette 24 and incorporates therein the radiation detector 40, the battery 44, the wireless power receiver 49, a controller 46a, and the transceiver 48, which are housed in a box-shaped casing 154 made of a material that is permeable to the radiation X. The controller 46a functions in substantially the same fashion as the cassette controller 46 of the electronic cassette 24, and has the feeding-state determining unit 107, and the first type signal generator (or the second type signal generator) 109.

A longitudinal rail 156 is mounted on a lower surface of the image capturing table 150. The radiation detecting apparatus 152 is movable to a desired position in the directions indicated by the arrow X (horizontal direction) along the rail 156 by a slider mechanism, not shown, mounted on the casing 154. Therefore, the radiation detecting apparatus 152 can be moved horizontally to a desired area to be imaged of the patient 14 lying on the image capturing table 150.

With the radiographic image capturing system 10c, the radiation detecting apparatus 152 is movable and incorporates the battery 44 and the wireless power receiver 49, as with the electronic cassette 24. Consequently, no power cable needs to be connected to the radiation detecting apparatus 152. The radiation detecting apparatus 152 can be moved smoothly without being limited by the power cable and hence can be handled with ease. As with the radiographic image capturing systems 10, etc, the radiographic image capturing system 10c is capable of suitably controlling the contactless (wireless) power feeding from the power feeder 25 to the battery 44 and the image capturing by the image capturing apparatus 22 for thereby acquiring radiographic images of high quality by performing the image-capturing inhibition control during the power-feeding period and the image-capturing start control during the non-power-feeding period.

As shown in FIG. 12, rollers 158 may be mounted on the lower ends of legs of the image capturing table 150. Therefore, the image capturing table 150 can easily be moved to a desired position. If necessary, the rail 156 may be dispensed with, and the radiation detecting apparatus 152 may be fixed to the image capturing table 150.

Figure 13:
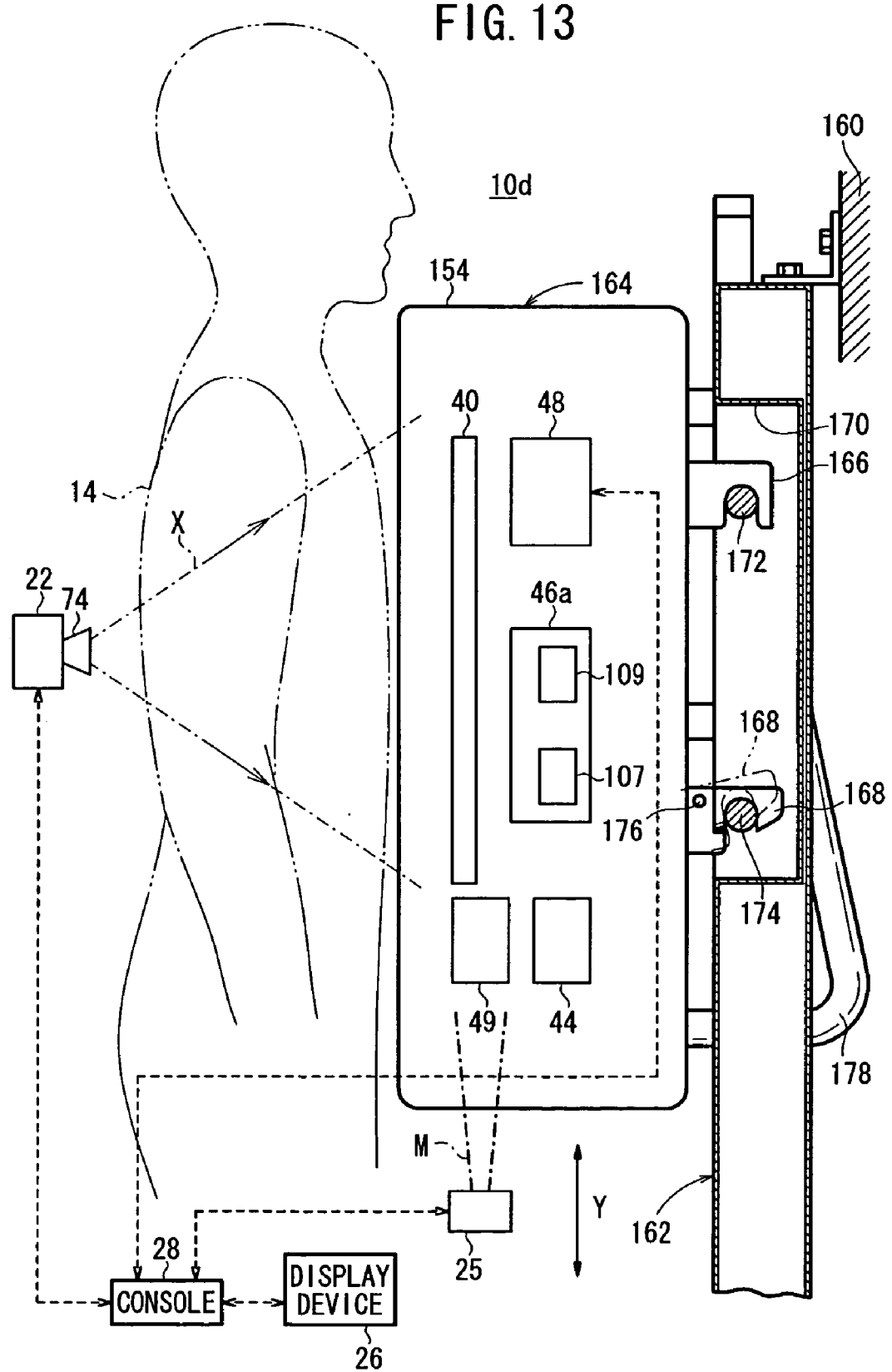
FIG. 13 is a side elevational view, partly in block form and cross section, of a radiographic image capturing system according to a fourth modification of the radiographic image capturing system shown in FIG. 4.

FIG. 13 is a side elevational view, partly in block form and cross section, of a radiographic image capturing system 10d according to a fourth modification of the radiographic image capturing system 10 shown in FIG. 4.

As with the radiographic image capturing system 10c, the radiographic image capturing system 10d does not employ the electronic cassette 24, but includes a radiation detecting apparatus 164 detachably mounted on a vertical post 162 fixed to a floor, not shown, and a wall 160, for capturing a radiographic image of the patient 14 while the patient 14 is upstanding.

The radiation detecting apparatus 164 is substantially the same in construction as the electronic cassette 24 and the radiation detecting apparatus 152 and incorporates therein the radiation detector 40, the battery 44, the wireless power receiver 49, the controller 46a, and the transceiver 48, which are housed in the box-shaped casing 154 made of a material that is permeable to the radiation X.

The radiation detecting apparatus 164, which functions as an upstanding image capturing table, has a pair of vertically spaced upper and lower hooks 166, 168 on a rear surface thereof which faces the post 162. The post 162 has a mounting recess 170 defined in a side surface thereof which faces the radiation detecting apparatus 164. A pair of vertically spaced upper and lower shafts 172, 174 for engaging the respective hooks 166, 168 are disposed in the mounting recess 170 and extend horizontally in transverse directions (shoulder-width direction) of the patient 14. The lower hook 168 is pivotally supported on a pivot shaft 176 for upward swinging movement about the pivot shaft 176 as indicated by the two-dot-and-dash lines in FIG. 13. The lower hook 168 is normally biased to turn downwardly by a spring mechanism, not shown, to stay in engagement with the lower shaft 174.

Since the hook 168 is swingably movable about the pivot shaft 176, the hooks 166, 168 can easily and reliably be brought into and out of hooking engagement with the respective shafts 172, 174, or in other words, the radiation detecting apparatus 164 can easily and reliably be mounted on and removed from the post 162. The radiation detecting apparatus 164 mounted on the post 162 can be moved vertically in the directions indicated by the arrows Y by a slide mechanism, not shown.

In FIG. 13, frames 178 are fixed to respective transverse ends of the casing 154. The frames 178 are in the form of rods to be gripped by the patient 14 when the patient 14 wants to take or keep a desired image capturing posture with respect to the radiation detecting apparatus 164.

With the image capturing system 10d, the radiation detecting apparatus 164 is removably mounted on and movable with respect to the post 162, and incorporates the battery 44 and the wireless power receiver 49 as with the electronic cassette 24 and the radiation detecting apparatus 152. Consequently, no power cable needs to be connected to the radiation detecting apparatus 164. The radiation detecting apparatus 164 can be moved and mounted and removed smoothly without being limited by the power cable. As with the radiographic image capturing systems 10 and the like, the radiographic image capturing system 10d is capable of suitably controlling the contactless (wireless) power feeding from the power feeder 25 to the battery 44 and the image capturing by the image capturing apparatus 22 for thereby acquiring radiographic images of high quality by performing the image-capturing inhibition control during the power-feeding period and the image-capturing start control during the non-power-feeding period.

Figure 14:
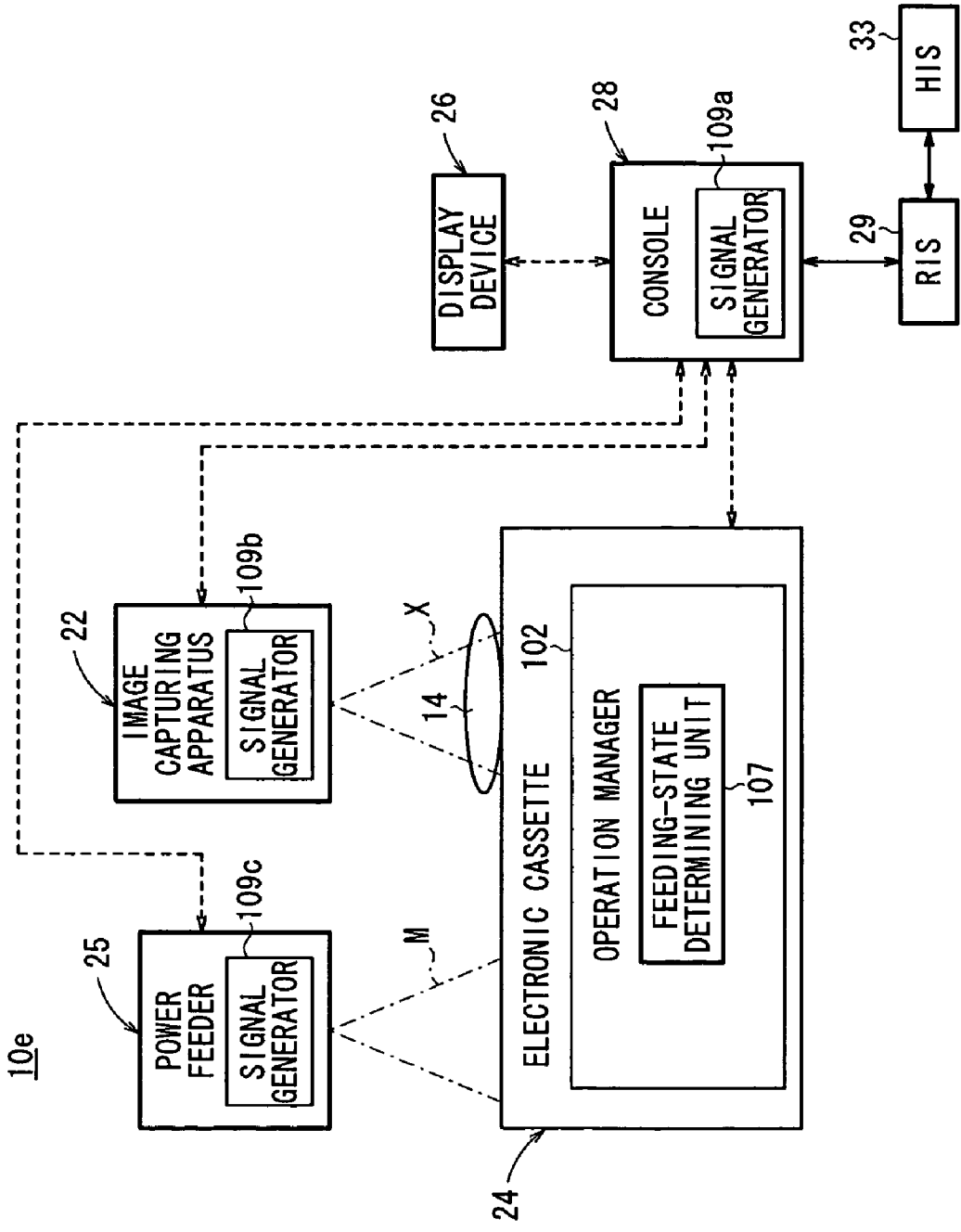
FIG. 14 is a schematic view of a radiographic image capturing system according to a fifth modification of the radiographic image capturing system shown in FIG. 4.

FIG. 14 is a schematic view of a radiographic image capturing system 10e according to a fifth modification of the radiographic image capturing systems 10, 10a shown respectively in FIGS. 4, 8.

The radiographic image capturing system 10e differs from the radiographic image capturing system 10, 10a (see FIGS. 4, 5 and 8) in that the operation manager 102 has the feeding-state determining unit 107 while the console 28, the image capturing apparatus 22 and the power feeder 25 have the signal generators 109a, 109b, 109c, respectively.

In FIG. 14, constituent elements other than the operation manager 102, the feeding-state determining unit 107 and the signal generators 109a, 109b, 109c in the electronic cassette 24, the console 28, the image capturing apparatus 22 and the power feeder 25 are not illustrated.

In FIG. 14, the console 28, the image capturing apparatus 22 and the power feeder 25 have the signal generators 109a, 109b, 109c, respectively. However, either one thereof may have a signal generator. That is, in the fifth modification, if the feeding-state determining unit and the signal generator are assigned to at least two apparatus (two of the image capturing apparatus 22, the electronic cassette 24, the power feeder 25 and the console 28), i.e., if the image-capturing-state determining unit is provided in one thereof and the signal generator is provided in another thereof, the same functions as the operation manager 102 shown in FIG. 5 can be performed.

In the image capturing system 10e of FIG. 14, the feeding-state determining unit 107 of the operation manager 102 recognize a state (operation mode depending on whether power-feeding is being performed or not) of the electronic cassette 24, and send a judgment result corresponding to the state, to the signal generators 109a, 109b, 109c. Then, the signal generators 109a, 109b, 109c determine the most appropriate image-capturing state (image-capturing permission, image-capturing inhibition) based on the sent operation mode (the judgment result), and generates a signal corresponding to the above most appropriate image-capturing state.

The image capturing system 10e according to the fifth modification can obtain the same advantageous effects as the image capturing system 10, 10a.

Figure 15:
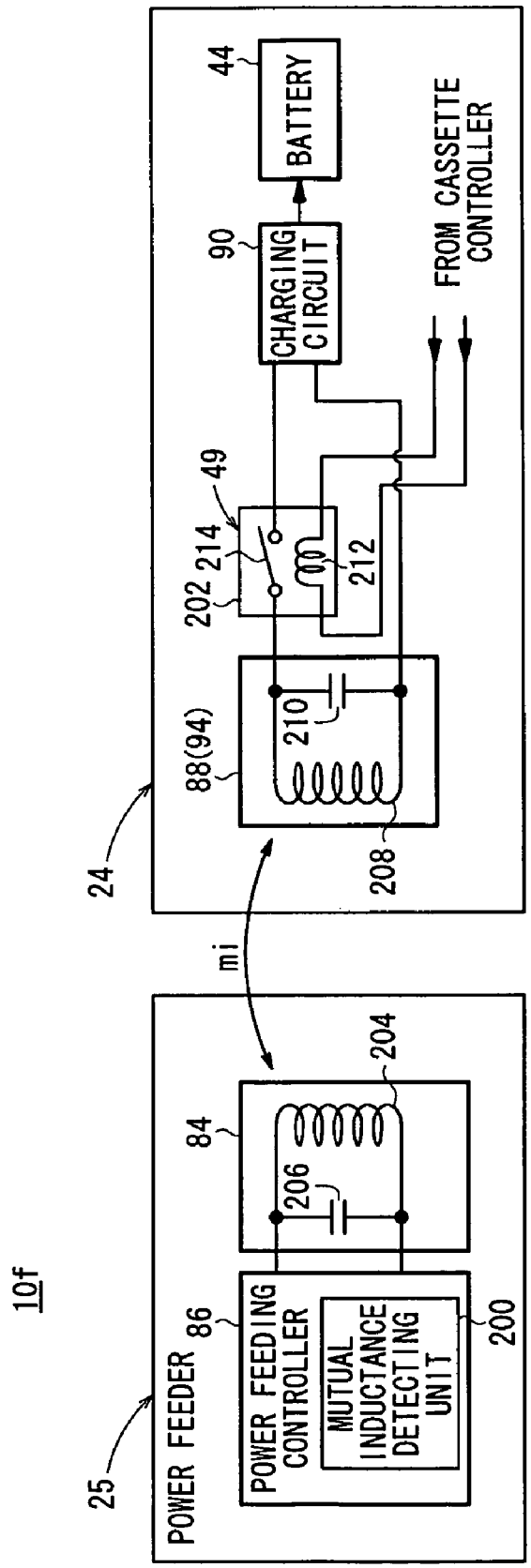
FIG. 15 is a schematic view of a radiographic image capturing system according to a sixth modification of the radiographic image capturing system shown in FIG. 4.

FIG. 15 is a schematic view of a radiographic image capturing system 10f according to a sixth modification of the radiographic image capturing system 10 shown in FIG. 4.

The image capturing system 10f differs from the image capturing system 10 (see FIGS. 4 and 5) in that the feeding controller 86 of the power feeder 25 has a mutual inductance detecting unit 200, and the wireless power receiver 49 has a relay 202. In FIG. 15, constituent elements other than the LC resonator 84 and the power feeding controller 86 of the power feeder 25, the battery 44 of the electronic cassette 24 and the wireless power receiver 49 are not illustrated.

In an example thereof, the LC resonator 84 of the power feeder 25 comprises an LC parallel resonant circuit having a coil 204 and a capacitor 206 that are connected together in parallel with each other, while the LC resonator 88 or the detecting LC resonator 94 of the electronic cassette 24 comprises an LC parallel resonant circuit having a coil 208 and a capacitor 210 that are connected together in parallel with each other. The relay 202 comprises an operation coil 212 to which the cassette controller 46 supplies a signal (electric current), and a contact-type switch 214 for performing ON-OFF action in response to excitation of the operation coil 212 by the electric current. The switch 214 has an end connected to the coil 208 and the capacitor 210, and the other end connected to the charging circuit 90.

When the cassette controller 46 judges that charging of the battery 44 is necessary and then applies electric current to the operation coil 212, the operation coil 212 generates magnetic flux based on the electric current, and magnetizes an electromagnet (not shown). As a result, the electromagnet attracts a piece of iron of the switch 214 to switch from an OFF-state to an ON-state. Thus, contactless power feeding by the power feeder 25 to the battery 44 is enabled.

On the other hand, while the contactless power feeding is being performed, the coil 204 of the LC resonator 84 and the coil 208 of the LC resonator 88 or the detecting LC resonator 94 are magnetically-coupled to each other through a mutual inductance mi.

In this state, if the cassette controller 46 determines stoppage (inhibition) of charging the battery 44 to stop energization of the operation coil 212, generation of magnetic flux by the operation coil 212 is halted. Accordingly, the piece of iron is separated away from the electromagnet, and the switch 214 is brought into an OFF-state. As a result, the electric connection between the coil 208, the charging circuit 90 and the battery 44 is cut off, and then the mutual inductance mi between the coil 204 and the coil 208 changes abruptly.

The mutual inductance detecting unit 200 detects electric current flowing through the coil 204. When the magnitude of the electric current changes temporally abruptly, the mutual inductance detecting unit 200 judges that the mutual inductance mi has changed abruptly due to switching of the switch 214 from an ON-state to an OFF-state.

When the mutual inductance detecting unit 200 detects an abrupt change of the mutual inductance mi, the feeding controller 86 judges that the cassette controller 46 has determined stoppage (inhibition) of charging the battery 44. Then, the feeding controller 86 stops supply of electric energy (high-frequency electric power) to the LC resonator 84.

In the image capturing system 10f according to the sixth modification, even if the feeding inhibition signal is not supplied for some reasons, the power feeder 25 can stop contactless power feeding based on detection of an abrupt temporal change of the mutual inductance mi by the mutual inductance detecting unit 200, thereby performing feeding control of the battery 44 accurately and reliably. Thus, the power feeder 25 can judge, on its own, whether power feeding to the battery 44 should be inhibited or not, even without supply of the feeding inhibition signal.

In the above explanations, if it is judged that the remaining power level of the battery 44 is sufficient, then a charging inhibition control is performed. When the remaining power level of the battery 44 is sufficient, the following charging inhibition control may be performed instead of the above charging inhibition control. That is, a power switch (not shown) is provided on a side surface of the electronic cassette 24. A surgeon (doctor) 18 or a technician operates the power switch to start image-capturing, and in response to the operation of the power switch, the charging inhibition control is performed.

With the radiographic image capturing systems 10 and 10a to 10f, the electronic cassette 24 and the radiation detecting apparatus 152, 164 are movable. Even when the electronic cassette 24 and the radiation detecting apparatus 152, 164 are set in a desired image capturing position, they can easily be supplied contactlessly with electric power by the power feeder 25. Since the electronic cassette 24 and the radiation detecting apparatus 152, 164 have the feeding-state determining unit 107 and the signal generator 109, it is possible to capture radiographic images of high quality without being adversely affected by noise caused by the contactless (wireless) power feeding, and also to quickly charge the battery 44 while no radiographic images are being captured, i.e., after the image capturing process has been finished or before the image capturing process is performed.

Although certain preferred embodiments of the present invention have been shown and described in detail, it should be understood that various changes and modifications may be made therein without departing from the scope of the appended claims.

What is claimed is:

1. A radiation detecting apparatus comprising:
   a radiation detector for detecting radiation transmitted through a subject and converting the detected radiation into radiographic image information;
   a power supply for supplying electric power to the radiation detector;
   a contactless power receiver for receiving electric power supplied contactlessly from an external contactless power feeder and supplying the received electric power to the power supply;
   a feeding-state determining unit for determining whether power-feeding by the contactless power feeder is being performed or not; and
   an image-capturing operation processing unit for performing a process for invalidating an operation for image-capturing by the radiation at least if the feeding-state determining unit judges that the power-feeding is being performed.

2. A radiation detecting apparatus according to claim 1, wherein the image-capturing operation processing unit generates an image-capturing inhibition signal for inhibiting the image-capturing by the radiation if the feeding-state determining unit judges that the power-feeding is being performed.

3. A radiation detecting apparatus according to claim 1, wherein the image-capturing operation processing unit does not generate an image-capturing permission signal for permitting the image-capturing by the radiation if the feeding-state determining unit judges that the power-feeding is being performed.

4. A radiation detecting apparatus according to claim 1, wherein the image-capturing operation processing unit generates an image-capturing permission signal for permitting the image-capturing by the radiation if the feeding-state determining unit judges that the power-feeding is not performed.

5. A radiographic image capturing system comprising:
   a radiation applying apparatus for applying radiation to a subject;
   a radiation detecting apparatus including a radiation detector for detecting the radiation transmitted through the subject and converting the detected radiation into radiographic image information, and a power supply for supplying electric power to the radiation detector;
   a contactless power feeder disposed in the radiation detecting apparatus, for supplying electric power contactlessly to a contactless power receiver which supplies electric power to the power supply;
   a controller for controlling the radiation applying apparatus, the radiation detecting apparatus, and the contactless power feeder;
   a feeding-state determining unit for determining whether power-feeding by the contactless power feeder is being performed or not;
   an image-capturing operation processing unit for performing a process for invalidating an operation for image-capturing by the radiation at least if the feeding-state determining unit judges that the power-feeding is being performed; and
   an image-capturing controller for controlling the radiation applying apparatus based on the process performed by the image-capturing operation processing unit.

6. A radiographic image capturing system according to claim 5, wherein the image-capturing operation processing unit generates an image-capturing inhibition signal for inhibiting the image-capturing by the radiation if the feeding-state determining unit judges that the power-feeding is being performed, and in case that the image-capturing controller receives the image-capturing inhibition signal, the image-capturing controller controls the radiation applying apparatus to inhibit the image-capturing.

7. A radiographic image capturing system according to claim 5, wherein the image-capturing operation processing unit does not generate an image-capturing permission signal for permitting the image-capturing by the radiation if the feeding-state determining unit judges that the power-feeding is being performed, and while the image-capturing controller does not receive the image-capturing permission signal, the image-capturing controller controls the radiation applying apparatus to inhibit the image-capturing.

8. A radiographic image capturing system according to claim 5, wherein the image-capturing operation processing unit generates an image-capturing permission signal for permitting the image-capturing by the radiation if the feeding-state determining unit judges that the power-feeding is not performed and in case that the image-capturing controller receives the image-capturing permission signal, the image-capturing controller controls the radiation applying apparatus to start the image-capturing or to be brought into an image-capturing stand-by state.

9. A radiographic image capturing system according to claim 5, wherein the feeding-state determining unit and the image-capturing operation processing unit are provided in at least one of the radiation applying apparatus, the radiation detecting apparatus, the contactless power feeder and the controller.

10. A radiographic image capturing system according to claim 5, wherein the image-capturing controller is provided in at least one of the radiation applying apparatus, the radiation detecting apparatus, the contactless power feeder, and the controller.

11. A radiographic image capturing system according to claim 6, further comprising a display device for displaying the radiographic image information and indicating the inhibition of the image capturing.

12. A radiographic image capturing system according to claim 11, wherein the display device indicates a present charged amount of the battery or a remaining charging time before the charged amount reaches an amount of electric power required for performing the image capturing.

13. A radiographic image capturing system according to claim 11, wherein the display device indicates that there is another radiation detecting apparatus that has already been charged to have the amount of electric power required for performing the image capturing.

14. A method of capturing a radiographic image of a subject by applying radiation to the subject, detecting the radiation with a radiation detector of a radiation detecting apparatus, and converting the detected radiation into radiographic image information with the radiation detector, comprising the steps of:

supplying electric power contactlessly to a power supply of the radiation detecting apparatus; and inhibiting image-capturing by the radiation while power-feeding is being performed.

15. A method of capturing a radiographic image according to claim 14, further comprising the step of starting the image-capturing after the power-feeding has been finished while the image-capturing is inhibited during the power-feeding.

* * * * *